(12) United States Patent
Casset et al.

(10) Patent No.: US 12,226,640 B2
(45) Date of Patent: Feb. 18, 2025

(54) SYSTEMS AND METHODS FOR NORMALIZING CARDIAC ELECTRICAL CONDITIONS OF MEASURED HEMODYNAMIC VARIATIONS FOR USE IN CARDIAC PACING DEVICE OPTIMIZATION PROCESSES

(71) Applicant: PACESETTER, INC., Sylmar, CA (US)

(72) Inventors: Cyrille Casset, Saint Selve (FR);
Louis-Philippe Richer, Montreal (FR);
Craig D. Markovitz, Leipzig (DE);
Jan Mangual-Soto, Rho (IT)

(73) Assignee: Pacesetter, Inc., Sylmar, CA (US)

( * ) Notice: Subject to any disclaimer, the term of this patent is extended or adjusted under 35 U.S.C. 154(b) by 588 days.

(21) Appl. No.: 15/701,209

(22) Filed: Sep. 11, 2017

(65) Prior Publication Data
US 2019/0076660 A1 Mar. 14, 2019

(51) Int. Cl.
| A61N 1/36 | (2006.01) |
| A61B 5/00 | (2006.01) |
| A61B 5/349 | (2021.01) |
| A61N 1/362 | (2006.01) |
| A61N 1/365 | (2006.01) |
| A61N 1/368 | (2006.01) |
| A61N 1/37 | (2006.01) |

(52) U.S. Cl.
CPC .......... *A61N 1/36585* (2013.01); *A61B 5/349* (2021.01); *A61B 5/4836* (2013.01); *A61B 5/686* (2013.01); *A61N 1/3627* (2013.01); *A61N 1/36842* (2017.08); *A61N 1/36843* (2017.08); *A61N 1/3706* (2013.01)

(58) Field of Classification Search
CPC ............ A61N 1/36564; A61N 1/36571; A61N 1/36578; A61N 1/3627; A61N 1/371; A61N 1/36514; A61N 1/3706
See application file for complete search history.

(56) References Cited

U.S. PATENT DOCUMENTS

| 2004/0147966 A1* | 7/2004 | Ding .................... A61N 1/3627 607/9 |
| 2004/0181260 A1* | 9/2004 | Anderson .............. A61B 5/083 607/17 |
| 2004/0220636 A1* | 11/2004 | Burnes ............... A61N 1/37254 607/17 |
| 2007/0078489 A1* | 4/2007 | Meyer .................... A61N 1/371 607/9 |

(Continued)

*Primary Examiner* — Sana Sahand
(74) *Attorney, Agent, or Firm* — Armstrong Teasdale LLP

(57) ABSTRACT

The present disclosure provides systems and methods for optimizing pacing parameters of a cardiac pacing device implanted in a patient. The systems and methods measure a plurality of hemodynamic responses of the patient. Each hemodynamic response is associated with the cardiac pacing device configured with one candidate pacing parameter set of a plurality of candidate pacing parameter sets. Each candidate pacing parameter set is classified as electrically equivalent to a reference pacing parameter set according to a classification criterion. The systems and methods further identify an optimal hemodynamic response from the plurality of hemodynamic responses, and select a final candidate pacing parameter set corresponding to the optimal hemodynamic response.

17 Claims, 8 Drawing Sheets

(56) References Cited

U.S. PATENT DOCUMENTS

| | | | |
|---|---|---|---|
| 2009/0082825 A1* | 3/2009 | Arcot-Krishnamurthy | A61N 1/3627 607/18 |
| 2009/0118783 A1* | 5/2009 | Patangay | A61N 1/3627 607/18 |
| 2009/0131999 A1* | 5/2009 | Li | A61N 1/36585 607/17 |
| 2009/0210024 A1* | 8/2009 | M. | A61B 5/4029 607/28 |
| 2010/0030295 A1* | 2/2010 | Whinnett | A61N 1/3627 607/30 |
| 2010/0125305 A1* | 5/2010 | Bornzin | A61N 1/36521 607/8 |
| 2010/0305638 A1* | 12/2010 | McCabe | A61N 1/3706 607/11 |
| 2011/0196441 A1* | 8/2011 | Ryu | A61N 1/3708 607/17 |
| 2012/0296388 A1* | 11/2012 | Zhang | A61B 7/005 607/18 |
| 2013/0030484 A1* | 1/2013 | Zhang | A61B 7/04 607/17 |
| 2013/0053716 A1* | 2/2013 | Zhang | A61N 1/3627 600/513 |
| 2013/0261473 A1* | 10/2013 | Xi | A61B 5/0215 600/486 |
| 2013/0289641 A1* | 10/2013 | Gustafsson | A61B 5/02028 607/18 |
| 2018/0042510 A1* | 2/2018 | Nakar | A61B 5/04012 |
| 2018/0250514 A1* | 9/2018 | Ghosh | A61N 1/3682 |

* cited by examiner

SYSTEMS AND METHODS FOR NORMALIZING CARDIAC ELECTRICAL CONDITIONS OF MEASURED HEMODYNAMIC VARIATIONS FOR USE IN CARDIAC PACING DEVICE OPTIMIZATION PROCESSES

FIELD OF THE DISCLOSURE

The present disclosure relates generally to systems and methods for optimizing the pacing parameters of an implanted cardiac pacing device, and more particularly to systems and methods for optimizing the pacing parameters of an implanted cardiac pacing device that includes normalizing cardiac electrical conditions associated with candidate pacing parameter sets to enhance the speed and quality of optimization of implantable cardiac pacing device programming.

BACKGROUND

Cardiac resynchronization therapy (CRT) is a technique for reducing the risk of heart failure by normalizing asynchronous cardiac electrical activation and the resultant asynchronous contractions by delivering synchronized pacing stimuli to both ventricles using a pacemaker or an implantable cardioverter-defibrillator (ICD) provided with biventricular pacing capability. During operation of the cardiac pacing device to provide CRT to a patient, the stimuli are synchronized so as to enhance overall cardiac performance of the patient. Pacing control parameters defining the operation of the cardiac pacing device, such as interventricular delay, typically need to be adjusted for each patient so as to synchronize the ventricles and to optimize the patient's cardiac performance in response to the CRT provided by the cardiac pacing device. Using existing pacing optimization methods, the optimization of interventricular delay values or other cardiac pacing control values is typically time consuming.

Cardiac pacing device programming is an important factor for maximizing the responder rate and patient outcome in cardiac resynchronization therapy (CRT). At least some existing methods for optimizing cardiac pacing devices are guided by hemodynamic measurements. One existing cardiac pacing device optimization method evaluates the effect of pacing control parameter values based on hemodynamic changes across pacing transitions between two different sets of pacing control parameter values that define different configurations of the cardiac pacing device. Other existing methods have attempted to increase the efficiency of cardiac pacing device optimization by focusing on three cardiac pacing device control parameters typically associated with the delivery of CRT: atrioventricular delay (AVD) representing the delay between the atrial event and the ventricular pacing spike; the site of stimulation by the cardiac pacing device, which may include single or multiple stimulation sites; and interventricular delays (VVD), representing the delay between all ventricular pacing spikes.

In existing automated methods of cardiac pacing device optimization described above, each of these three pacing control factors is typically optimized separately by optimizing each parameter individually. For example, the influence of changes in AVD value on the patient's hemodynamic response may be assessed while keeping the site of stimulation by the cardiac pacing device and VVD value constant. The influence of each parameter on a recorded hemodynamic response of the patient are used to define individually an optimal AVD value, optimal site of stimulation, and optimal VVD value. The cardiac pacing device is programmed to enable the individually optimized AVD value, site of stimulation, and VVD value, based on the assumption that the linear superposition of individually optimized cardiac pacing device pacing parameters results in an optimized overall hemodynamic response to the CRT provided by the cardiac pacing device.

However, the benefits of a cardiac pacing device optimized individually as described above are likely to be diminished if the effect of variations in any one pacing parameter influences the effect of variations in any of the other pacing parameters. By way of non-limiting example, during individual optimization of AVD with site of stimulation and VVD fixed, the identified optimum may vary for different sites of stimulation and VVD values. If the individually optimized site of stimulation and VVD value are not matched to the fixed values used in the AVD optimization, the individually optimized AVD value combined with individually optimized site of stimulation and VVD value may not result in an optimized hemodynamic response. By way of another non-limiting example, the benefit of an individually optimized pacing site configuration is not linearly distributed along AVD range, and the optimal AVD value must be adapted to the selected pacing site configuration. By way of another additional non-limiting example, the individually optimized pacing vector influences the time of intraventricular electrical conduction and ultimately influences the mechanical time between ventricular stimulation and aortic ejection.

At least several known properties of the response of the heart to exogenous stimulation indicate that at least some of the CRT pacing parameters do not influence overall hemodynamic performance independently. For example, it is known that the benefit of a pacing site configuration is not linearly distributed along a range of AVD values typically used in CRT, and as a result the optimal AVD is typically adapted to the pacing site configuration tested. In addition, it is known that the choice of pacing vector affects the time of intraventricular electrical conduction which, ultimately, influences the mechanical time between ventricular stimulation and aortic ejection.

In order to ameliorate the impact of the interdependence of the CRT pacing parameters on overall hemodynamic performance of the patient, additional evaluations to assess the effect of variations of each CRT control parameter with different combinations of the remaining CRT control parameters held constant may be conducted. However, these additional assessments essentially eliminate the enhanced efficiency of cardiac pacing device optimization afforded by automation of the optimization method.

BRIEF SUMMARY OF THE DISCLOSURE

In one embodiment, the present disclosure is directed to a method for optimizing pacing parameters of a cardiac pacing device implanted in a patient. The method includes measuring a plurality of hemodynamic responses of the patient, with each hemodynamic response associated with the cardiac pacing device configured with one candidate pacing parameter set of a plurality of candidate pacing parameter sets of the cardiac pacing device. Each candidate pacing parameter set is classified as electrically equivalent to a reference pacing parameter set according to a classification criterion. The method also includes identifying an optimal hemodynamic response from the plurality of hemodynamic responses, and selecting a final candidate pacing parameter set corresponding to the optimal hemodynamic response.

In another embodiment, the method further includes selecting a reference pacing parameter set and a variable pacing parameter set that includes a plurality of values of one pacing parameter. The reference pacing parameter set includes one value of the variable pacing parameter set. The method further includes measuring a reference ECG of the patient in which the reference ECG is associated with the cardiac pacing device configured with the reference pacing parameter set. In addition, the method includes measuring a series of baseline ECGs, in which each baseline ECG of the series is associated with the cardiac pacing device configured with the reference pacing parameter set and each value of the variable pacing parameter set. The method additionally includes determining a series of baseline correlation coefficients, in which each baseline correlation coefficient is indicative of each correlation between each baseline ECG of the series and the reference ECG. Additionally, the method includes selecting the threshold correlation coefficient. Each baseline ECG associated with each baseline correlation coefficient greater than the threshold correlation coefficient is classified as electrically equivalent to the reference ECG.

In an additional embodiment, the method further includes selecting a plurality of test pacing parameter sets. Each test pacing parameter set includes at least one test pacing parameter and one value of the variable pacing parameter set. The method also includes measuring a series of test ECGs, in which each test ECG of the series is associated with the cardiac pacing device configured with one test pacing parameter set. The method additionally includes determining a series of test correlation coefficients, in which each test correlation coefficient is indicative of each correlation between each test ECG of the series and the reference ECG. In addition, the method includes selecting one candidate pacing parameter set from the plurality of test pacing parameter sets. The one candidate pacing parameter set is a test pacing parameter set of the plurality associated with the minimum test correlation coefficient of the series that is greater than the threshold correlation coefficient.

In another embodiment, the present disclosure is directed to a system for optimizing pacing parameters of a cardiac pacing device implanted in a patient. The system includes an external hemodynamic sensing system configured to measure a plurality of hemodynamic responses of the patient associated with the cardiac pacing device configured with one candidate pacing parameter set of a plurality of candidate pacing parameter sets of the cardiac pacing device of the patient. The system also includes an external programmer in communication with the cardiac pacing device and the external hemodynamic sensing system. The external programmer includes a CPU and a computer-readable media encoded with a plurality of modules. Each module includes a set of instructions executable on the CPU. The plurality of modules includes a parameter optimizer controller configured to configure the cardiac pacing device with each of a plurality of candidate pacing parameter sets. Each of the plurality of candidate pacing parameter sets is classified as electrically equivalent to a reference pacing parameter set according to a classification criterion. The parameter optimizer controller is further configured to receive each of a plurality of hemodynamic responses of the patient associated with each candidate pacing parameter set from the external hemodynamic sensing system, identify an optimal hemodynamic response from the plurality of hemodynamic responses, and to select a final candidate pacing parameter set corresponding to the optimal hemodynamic response.

In another embodiment, the system further includes an external ECG sensing system in communication with the external programmer. The external ECG sensing system is configured to measure ECGs of the patient. The parameter optimizer controller is further configured to configure the cardiac pacing device with the reference fixed pacing parameter set and to receive a reference ECG of the patient from the external ECG sensing system. The reference ECG is associated with the cardiac pacing device configured with the reference pacing parameter set. The parameter optimizer controller is also configured to configure the cardiac pacing device with the reference pacing parameter set and each of a plurality of variable pacing parameter values and to receive a series of baseline ECGs from the external ECG sensing system, in which each baseline ECG of the series is associated with the cardiac pacing device configured with the reference pacing parameter set and each value of the variable pacing parameter set. The parameter optimizer controller is additionally configured to determine a series of baseline correlation coefficients, in which each baseline correlation coefficient is indicative of each correlation between each baseline ECG of the series and the reference ECG. In addition, the parameter optimizer controller is configured to select a threshold correlation coefficient. Each baseline ECG associated with each baseline correlation coefficient greater than the threshold correlation coefficient is classified as electrically equivalent to the reference ECG.

The foregoing and other aspects, features, details, utilities and advantages of the present disclosure will be apparent from reading the following description and claims, and from reviewing the accompanying drawings.

BRIEF DESCRIPTION OF THE DRAWINGS

The figures described below illustrate various aspects of the disclosure.

Corresponding reference characters indicate corresponding parts throughout the several views of the drawings.

DETAILED DESCRIPTION OF THE DISCLOSURE

Figure 1:
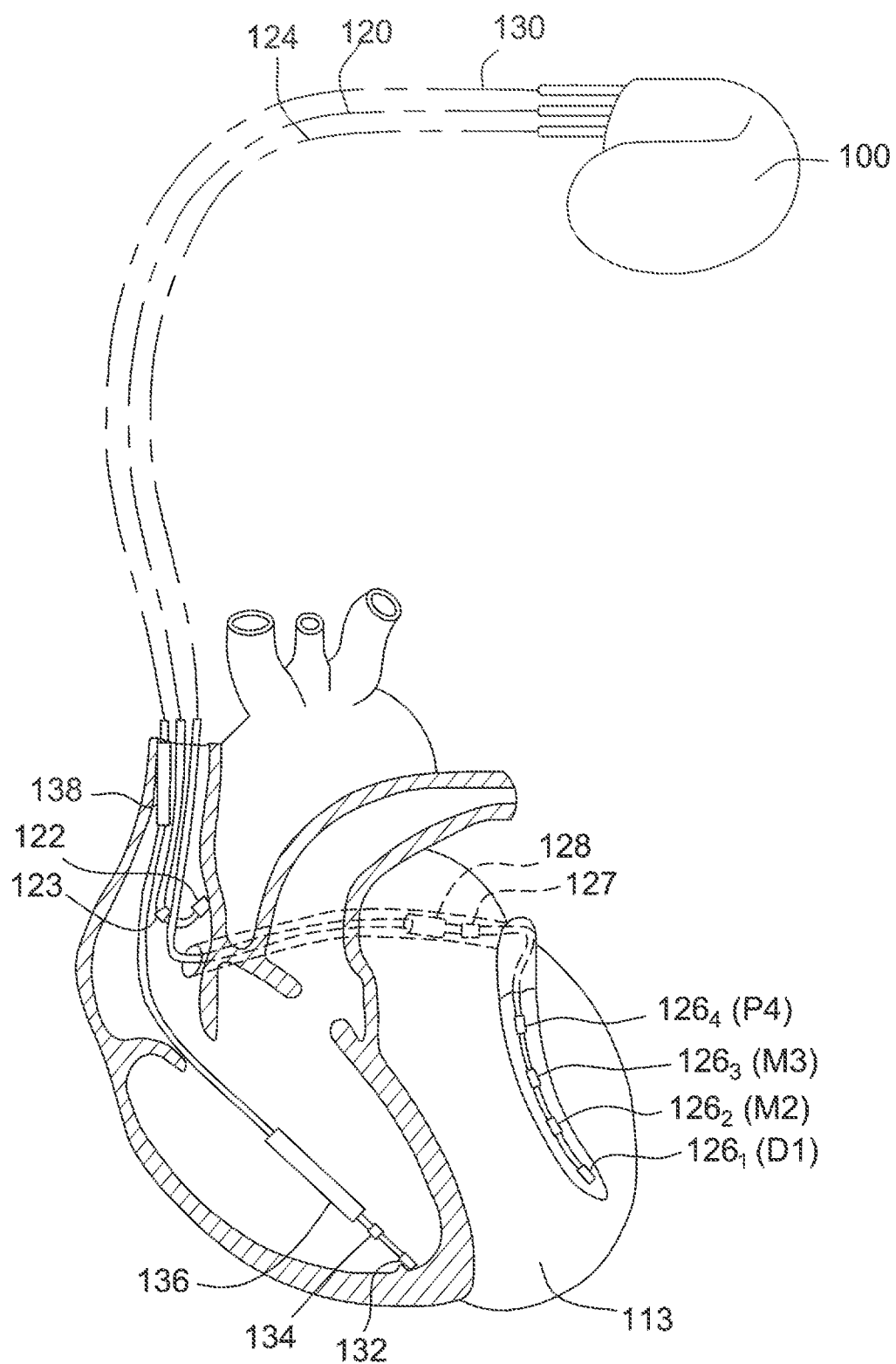
FIG. 1 is a schematic illustration of an implantable cardiac pacing device in electrical communication with at least three leads implanted into a patient's heart for delivering multi-chamber stimulation and shock therapy and sensing cardiac activity.

In various aspects, systems and methods for cardiac pacing device optimization are provided that include a method for pre-screening candidate pacing control parameters that identifies a dedicated AVD adapted at each pacing parameter configuration relative to a reference configuration. In various aspects, the disclosed pre-screening method makes use of ECG measurements, rather than hemodynamic measurements, to assess changes in cardiac performance for various combinations of pacing control parameters, thereby decreasing the overall duration of cardiac pacing device optimization. In various aspects, the pre-screening method assesses various combinations of pacing parameter settings using relatively rapid ECG measurements to identify a relatively small number of combinations of pacing parameter values to be assessed using hemodynamic measurements according to existing cardiac pacing device optimization methods.

In various aspects, the disclosed method for pre-screening candidate cardiac pacing control parameters overcomes limitations of existing cardiac pacing device optimization methods. The disclosed method identifies combinations of cardiac pacing parameters that correspond to comparable cardiac electrical conditions, resulting in the optimization of each individual cardiac pacing parameter under normalized conditions (i.e. comparable cardiac electrical conditions), thereby eliminating at least a portion of uncertainty associated with the interdependence of effects of various cardiac pacing parameters on hemodynamic performance. In one aspect, the normalized conditions are selected to be a common level of ECG correlation for different sets of cardiac pacing parameters relative to an identifiable reference condition including, but not limited to, fusion or 90% matching of an ECG (i.e. correlation coefficient of 0.9) to an ECG obtained using a short AVD value.

In various aspects, the level of electrical correlation obtained by comparing ECG measurements obtained under different sets of cardiac pacing control parameters is used to identify a reference condition or to indicate that normalized cardiac electrical conditions have been reached for a given ventricular pacing configuration defined by cardiac pacing parameters including, but not limited to, pacing vectors, number of vectors, and VV delay relative to a predefined reference ICD configuration including, but not limited to an RV only pacing site or AOO mode. In one aspect, the ECG-defined reference condition for each candidate cardiac pacing parameter set defines a consistent basis for the comparison of the effects of the candidate cardiac pacing parameter sets on hemodynamic response as assessed by hemodynamic measurements. Knowing that the electrical conditions for a first cardiac pacing parameter set are similar to a reference electrical condition, the hemodynamic response of this first cardiac pacing parameter set can be noted and compared with hemodynamic response from other cardiac pacing parameter sets assessed when the same electrical event was reached, reducing the need for additional assessments to correct for the effects of interdependence of various individual cardiac pacing parameter on hemodynamic response. In various aspects, the hemodynamic responses from two or more candidate cardiac pacing parameter sets corresponding to the reference electrical condition identified using the disclosed pre-screening method may be compared and the candidate cardiac pacing parameter set associated with an optimal hemodynamic response may be selected for additional optimization of the AVD of the cardiac pacing device using existing methods.

I. Cardiac Pacing Devices

The present disclosure provides systems and methods for systems and methods for cardiac pacing device optimization that include a method for pre-screening candidate cardiac pacing control parameters prior to selection and additional optimization of a candidate cardiac pacing parameter set corresponding to the optimal hemodynamic response. In various aspects, the cardiac pacing device provided with a cardiac pacing parameter set selected using the disclosed optimization methods is suitable for cardiac resynchronization therapy treatment of patients with a variety of cardiac electric disorders including, but not limited to, spontaneous atrio-ventricular conduction, bundle branch block, AV heart block type I, AV heart block type II, and paroxysmal AV heart block type III.

Any suitable known implantable cardiac device may be optimized using the disclosed systems and methods for cardiac pacing device optimization without limitation including, but not limited to, pacemakers and implantable cardioverter-defibrillators (ICDs) provided with biventricular pacing capability. In various aspects, an implantable cardiac pacing device includes a plurality of electrodes and a controller communicatively coupled to the plurality of electrodes. The controller is configured to cause the plurality of electrodes to apply a cardiac pacing therapy including, but not limited to, CRT to a patient's heart, to determine that the patient's heart is experiencing symptoms of one or more of the cardiac electric disorders described above, and to adjust at least one parameter of the cardiac pacing therapy based on this determination.

FIG. 1 is a schematic illustration of a pacemaker/implantable cardioverter-defibrillator device (ICD) device 100 suitable for use as a cardiac pacing device, and that is further compatible with the cardiac pacing device optimization methods disclosed herein. In one aspect, the cardiac pacing device 100 is a multi-site pacing device capable of treating both fast and slow arrhythmias with stimulation therapy, including cardioversion, defibrillation, and pacing stimulation, including multipoint pacing (MPP). To provide atrial chamber pacing stimulation and sensing, the cardiac pacing device 100 in this aspect is in electrical communication with a heart 113 by way of a right atrial (RA) lead 120 having an atrial tip electrode 122 and an atrial ring electrode 123 implanted in the atrial appendage. The pacemaker/ICD device 100 is also in electrical communication with heart 113 by way of a right ventricular (RV) lead 130 having, in this embodiment, a ventricular tip electrode 132, an RV ring electrode 134, an RV coil electrode 136, and a superior vena cava (SVC) coil electrode 138. Typically, the RV lead 130 is transvenously inserted into the heart so as to place the RV coil electrode 136 in the RV apex, and the SVC coil electrode 138 in the superior vena cave. Accordingly, the RV lead 130 is capable of receiving cardiac signals, and delivering stimulation in the form of pacing and shock therapy to the right ventricle (also referred to as the RV chamber).

To sense left atrial and ventricular cardiac signals and to provide left chamber pacing therapy, the cardiac pacing device 100 is coupled to a multi-pole left ventricular (LV) lead 124 designed for placement in the "CS region" for positioning a distal electrode adjacent to the left ventricle and/or additional electrode(s) adjacent to the left atrium (also referred to as the LA chamber). As used herein, the phrase "CS region" refers to the venous vasculature of the left ventricle, including any portion of the coronary sinus (CS), great cardiac vein, left marginal vein, left posterior ventricular vein, middle cardiac vein, small cardiac vein, and/or any other cardiac vein accessible by the CS. In one aspect, the LV lead 124 is configured to receive atrial and ventricular cardiac signals and to deliver left ventricular pacing therapy using a set of four LV electrodes $126_1$, $126_2$, $126_3$, and $126_4$ (thereby providing a quadra-pole lead), left atrial pacing therapy using at least a LA ring electrode 127, and shocking therapy using at least an LA coil electrode 128. In some embodiments, the LV lead 124 includes LV electrodes $126_1$, $126_2$, $126_3$, and $126_4$, but does not include the LA ring and coil electrodes 127 and 128. Non-limiting examples of suitable LV leads 124 include a Quartet™ left ventricular pacing lead (Abbott, USA), which includes four pacing electrodes on the left ventricular lead that enables up to ten pacing configurations.

The LV electrode $126_1$ is shown as being the most "distal" LV electrode with respect to the separation of the LV electrodes from the connection of the LV lead 124 to the cardiac pacing device 100. In one non-limiting example, the LV electrode $126_1$ is located at the apex of the left ventricle. The LV electrode $126_4$ is shown as being the most "proximal" LV electrode. For example the LV electrode $126_4$ may be located at the base of the left ventricle. The LV electrodes $126_2$ and $126_3$ are shown as being "middle" LV electrodes, between the distal and proximal LV electrodes $126_1$ and $126_4$. Accordingly, the four LV electrodes $126_1$, $126_2$, $126_3$, and $126_4$ are referred to respectively as the electrodes D1, M2, M3 and P4 in one aspect (where "D" stands for "distal", "M" stands for "middle" and "P" stands from "proximal", and the numbers are arranged from most distal to most proximal). In various other aspects, more or fewer LV electrodes are provided with the LV lead 124. For purposes of describing the cardiac pacing device 100 herein, it will be assumed that the multi-pole LV lead 124 includes the four LV electrodes $126_1$, $126_2$, $126_3$, and $126_4$, corresponding to the LV electrodes D1, M2, M3 and P4, respectively.

The LV electrodes $126_1$, $126_2$, $126_3$, and $126_4$ are configured to provide various pacing vectors and sensing vectors. In various aspects, at least a portion of the various pacing vectors and sensing vectors are intraventricular LV vectors, defined herein as vectors between two LV electrodes. In various other aspects, another portion of the various pacing vectors and sensing vectors are interventricular vectors, defined herein as vectors between one of the LV electrodes D1, M2, M3 and P4 and the RV coil electrode 136. Non-limiting examples of exemplary vectors suitable pacing and/or sensing using the LV electrodes D1, M2, M3 and P4 with and without the RV coil electrode 136 are listed in Table 1 below. As shown in Table 1, a first electrode in each vector is electrically connected to a cathode, and a second electrode in each vector is electrically connected to an anode. In some aspects, the electrical connections of the electrodes of a vector may be reversed, in particular those vectors in which neither electrode is a coil.

TABLE 1

Pacing and Sensing Vectors

| Pacing/Sensing Vector | Cathode | Anode |
| --- | --- | --- |
| 1 | D1 | RV coil |
| 2 | M2 | RV coil |
| 3 | M3 | RV coil |
| 4 | P4 | RV coil |
| 5 | D1 | M2 |
| 6 | D1 | P4 |
| 7 | M2 | P4 |
| 8 | M3 | M2 |
| 9 | M3 | P4 |
| 10 | P4 | M2 |

The other aspects, alternative and/or additional vectors, other than those listed above in Table 1 are used for pacing and/or sensing by the cardiac pacing device 100. Although only three leads are shown in FIG. 1, it is to be understood that the cardiac pacing device 100 may include additional leads with additional electrodes including, but not limited to, additional pacing, sensing, and shocking electrodes. In other additional aspects, additional electrodes are provided on the three leads illustrated in FIG. 1 including, but not limited to, additional electrodes on the RV or LV leads. In additional aspects, the cardiac pacing device 100 includes one lead or two leads.

Figure 2A:
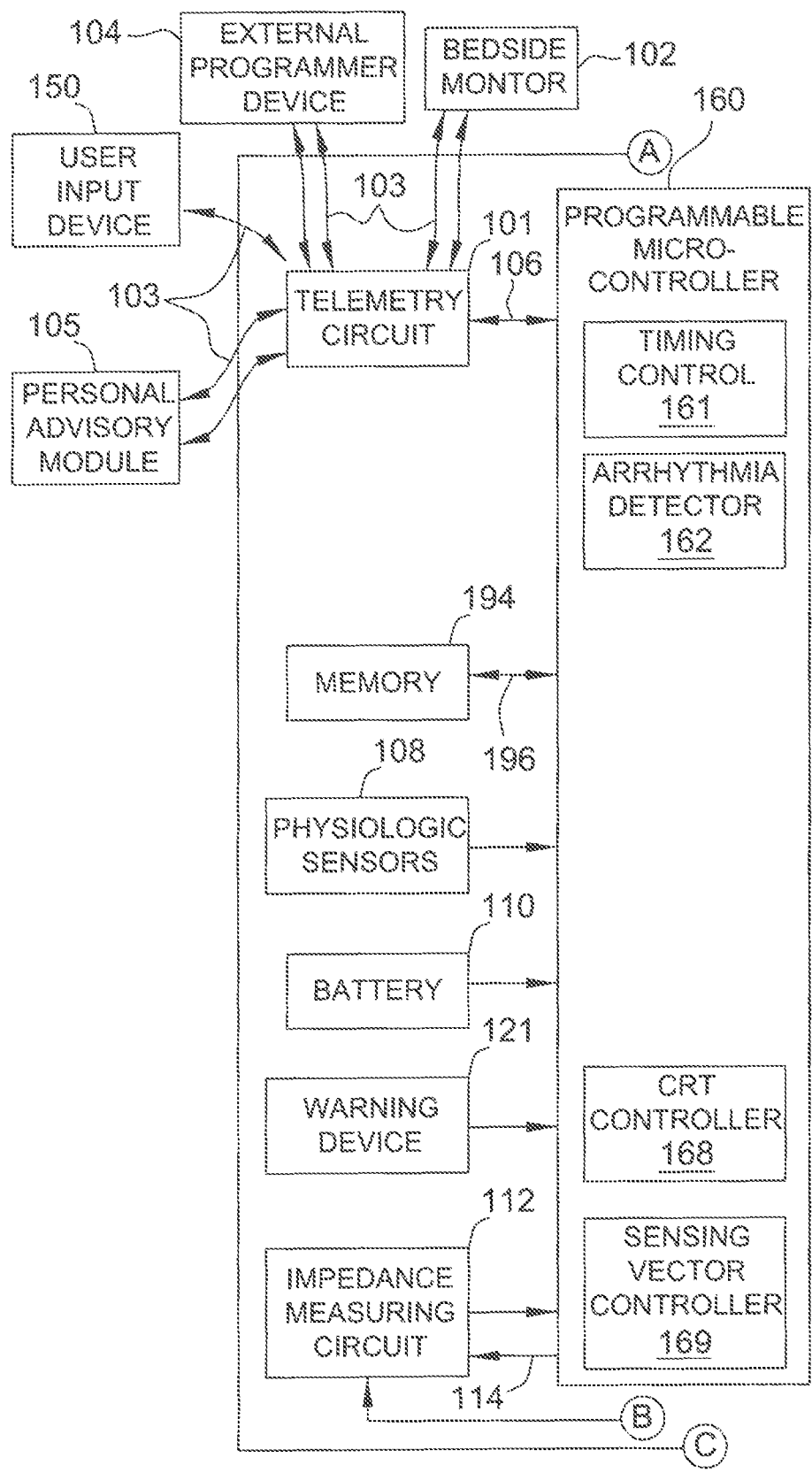
FIGS. 2A and 2B are a functional block diagram of the multi-chamber implantable cardiac pacing device of FIG. 1, illustrating the arrangement of elements that provide pacing stimulation, cardioversion, and defibrillation in four chambers of the heart.
Figure 2B:
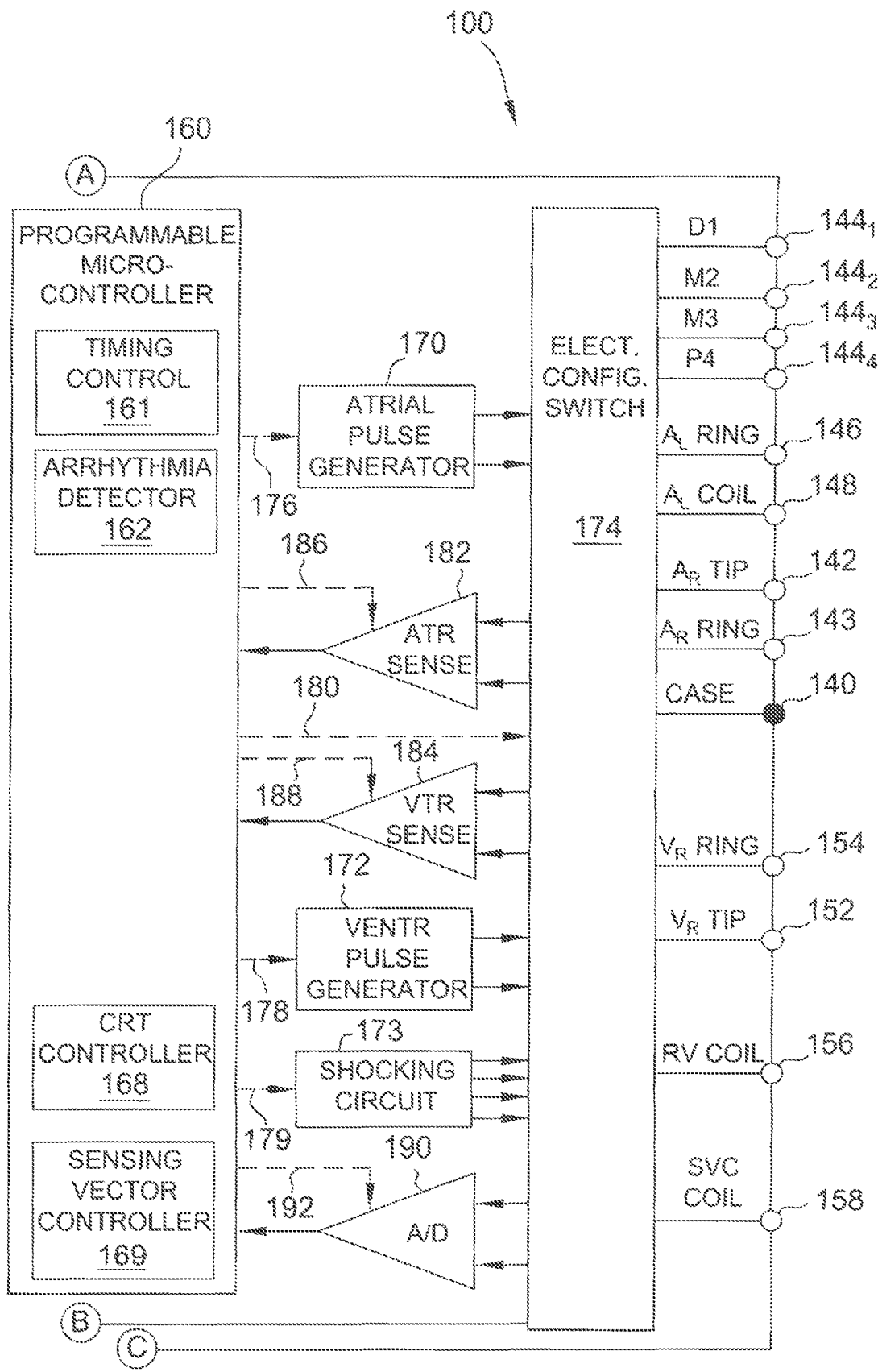

A simplified block diagram of internal components of the cardiac pacing device 100 is shown in FIGS. 2A and 2B (collectively referred to herein as FIG. 2). The particular cardiac pacing device 100 of FIG. 2 is shown for illustration purposes only, and one of skill in the art could readily duplicate, eliminate or disable the appropriate circuitry in any desired combination to provide a cardiac pacing device 100 configured to deliver a treatment to the appropriate chamber(s) of the heart 113. Non-limiting examples of treatments suitable for delivery by the cardiac pacing device 100 include cardioversion, defibrillation and pacing stimulation.

In various aspects, the cardiac pacing device 100 includes a housing 140, shown schematically in FIG. 2, also referred to as a "can", a "case" or a "case electrode". In other aspects, the housing 140 is configured to function as a return electrode for all "unipolar" modes, as illustrated in FIG. 2. The housing 140 may further be configured to function as a return electrode alone or in combination with one or more of coil electrodes including, but not limited to, electrodes 128, 136 and 138 for purposes of administering a shocking electrical treatment to the heart of the patient. The housing 140 further includes a connector (not shown) having a plurality of terminals 142, 143, $144_1$, $144_2$, $144_3$, $144_4$, 146, 148, 152, 154, 156 and 158, shown schematically in FIG. 2 and labeled with the names of the electrodes to each terminal of the plurality of terminals is connected.

In an aspect, to enable RA sensing and pacing, the connector includes at least an RA tip terminal 142 ($A_R$ TIP) configured to form an electrical connection to the atrial tip electrode 122 and an RA ring ($A_R$ RING) terminal 143 configured to form an electrical connection to the atrial ring electrode 123 via the right atrial (RA) lead 120. In another aspect, to enable left chamber sensing, pacing, and shocking, the connector further includes an LV tip terminal $144_1$ adapted for connection to the D1 electrode and additional LV electrode terminals $144_2$, $144_3$ and $144_4$ terminals adapted for connection to the M2, M3 and P4 electrodes, respectively, of the quadra-pole LV lead 124.

In other aspects, the connector further includes an LA ring terminal ($A_L$ RING) 146 and an LA shocking terminal ($A_L$ COL) 148, which are configured to form electrical connections to the LA ring electrode 127 and to the LA coil ($A_L$ COIL) electrode 128, respectively of the quadra-pole LV lead 124. To support right chamber sensing, pacing and shocking, the connector further includes an RV Up terminal ($V_R$ TIP) 152, an RV ring terminal ($V_R$ RING) 154, an RV shocking terminal ($V_R$ COIL) 156, and an SVC shocking terminal (SVC COIL) 158, configured to form electrical connections to the ventricular tip electrode 132, the RV ring electrode 134, the RV coil electrode 136, and the SVC coil electrode 138, respectively, of the right ventricular (RV) lead 130.

In various aspects, the cardiac pacing device 100 further includes an electrode configuration switch 174 configured to connect the desired electrodes to the appropriate I/O circuits of the cardiac pacing device 100 as described below, thereby enabling complete electrode programmability. In one aspect, the electrode configuration switch 174 includes a plurality of switches configured to selectively open and close in response to at least one control signal including, but not limited to, a control signal 180 from the microcontroller 160. In one aspect, the switch 174, in response to a control signed 180 from the microcontroller 160, determines the polarity of the stimulation pulses by selectively closing the appropriate combination of switches (not shown) as is known in the art. Non-limiting examples of polarities of the stimulation pukes determined by the switch 174 include unipolar, bipolar, and combipolar, defined herein as using unipolar leads in the atrium and ventricle and performing atrial sensing in a bipolar way using the ventricular lead tip as an indifferent electrode. In various additional aspects, the switch 174 also switches among the various LV electrodes.

In another aspect, the cardiac pacing device 100 includes a programmable microcontroller 160 configured to control various modes of stimulation therapy. As is well known in the art, the microcontroller 160 (also referred to herein as a control unit or controller) typically includes a microprocessor or equivalent control circuitry designed specifically for controlling the delivery of stimulation therapy and may further include RAM or ROM memory, logic and timing circuitry, state machine circuitry, and I/O circuitry. Typically, the microcontroller 160 is configured to process and/or monitor input signals (data) as controlled by a program code stored in a designated block of memory. In one aspect, the microcontroller 160 is coupled to and/or in communication with a plurality of circuits and devices including, but not limited to, a variety of pulse generation and shocking circuits configured to generate electrical pulses to be delivered to the heart, sensing circuits configured to monitor various aspects of electrical activity of the heart, various additional physiological sensors, and a plurality of various data input, output, and storage devices, described in additional detail below.

In various aspects, the microcontroller 160 is configured to control the delivery of pulses by various electrodes within the heart 113 via the right atrial (RA) lead 120, the left ventricular (LV) lead 124, and the right ventricular (RV) lead 130. The cardiac pacing device 100 further includes an atrial pulse generator 170, a ventricular pulse generator 172, and a shocking circuit 173 configured to receive the control signals 176, 178, and 179, respectively, delivered by the microcontroller 160. The atrial pulse generator 170 and the ventricular pulse generator 172 are configured to generate pacing stimulation pulses for delivery by the electrodes associated with the RA lead 120, the RV lead 130, and/or the LV lead 124, as described above, via an electrode configuration switch 174. In various aspects, the atrial pulse generator 170 and the ventricular pulse generator 172 are provided with any arrangement of known pulse generators including, but not limited to, dedicated and independent pulse generators, multiplexed pulse generators, shared pulse generators, and any combination thereof, to provide stimulation therapy in any one or more of the four chambers of the patient's heart. In various aspects, the control signals 176 and 178 produced by the microcontroller 160 are configured to trigger or inhibit the stimulation pulses produced by the atrial pulse generator 170 and the ventricular pulse generator 172, respectively.

In the case where the cardiac pacing device 100 is intended to operate as an implantable cardioverter/defibrillator (ICD) device, the cardiac pacing device 100 is configured to detect the occurrence of an arrhythmia, and to automatically apply an appropriate electrical shock therapy to the heart aimed at terminating the detected arrhythmia. In one aspect, the cardiac pacing device 100 further includes a shocking circuit 173 to enable the operation of the device 100 as an implantable cardioverter/defibrillator (CD) device by detecting the occurrence of an arrhythmia, and automatically applying an appropriate electrical shock therapy to the heart aimed at terminating the detected arrhythmia. In one aspect, the shocking circuit 173 is configured to generate shocking pulses for delivery by the RA lead 120, the RV lead 130, and/or the LV lead 124 via the electrode configuration switch 174. In this aspect, the shocking circuit 173 is configured to receive a control signal 179 from the microcontroller 160 and is further configured to produce the shocking pulses in response to the control signal 179. The shocking pulses produced by the shocking circuit 173 are modulated by the control signal 179 to an energy level including, but not limited to, a low energy level (up to 0.1 joules), a moderate energy level (0.1-10 joules) and a high energy level (11 to 40 joules or more). The shocking pulses are applied to the heart of the patient through at least two shocking electrodes selected from the LA coil electrode 128, the RV coil electrode 136, and the SVC coil electrode 138. In one aspect, the housing 140 may act as an active electrode in combination with the RV coil electrode 136, or as part of a split electrical vector using the SVC coil electrode 138 or the LA coil electrode 128 (i.e., using the RV coil electrode 136 as a common electrode).

In various aspects, the cardiac pacing device 100 includes an atrial sensing circuit 182 and a ventricular sensing circuit 184 configured to detect the presence of cardiac activity in each of the four chambers of the heart. In one aspect, the atrial sensing circuit 182 and the ventricular sensing circuit 184 are selectively coupled to the RA lead 120, LV lead 124, and RV lead 130 via the electrode configuration switch 174. As illustrated in FIG. 2, the outputs of the atrial sensing circuit 182 and the ventricular sensing circuit 184 are delivered to the microcontroller 160 to monitor cardiac activity in the chambers of the heart.

The elements of the atrial sensing circuit 182 and the ventricular sensing circuit 184 are controlled by the control signals 186 and 188, respectively. In one aspect, the atrial sensing circuit 182 and the ventricular sensing circuit 184 are configured to enable the programming of the sensing polarity independently of the programming of stimulation polarity by a clinician. In this aspect, the electrode configuration switch 174 is configured to determine the "sensing polarity" of the cardiac signal by selectively closing the appropriate switches, as is known in the art.

In additional aspects, the atrial sensing circuit 182 and the ventricular sensing circuit 184 include one or more amplifiers (not shown) including, but not limited to, dedicated sense amplifiers, multiplexed amplifiers, shared amplifiers, and any combination thereof. In one aspect, the one or more amplifiers include low power, precision amplifiers with programmable gain and/or automatic gain control, bandpass filtering, and a threshold detection circuit, as known in the art, to selectively sense the cardiac signal of interest. The automatic gain control of the amplifier in this aspect enables the cardiac pacing device 100 to effectively sense the low amplitude signals characterizing atrial or ventricular fibrillation.

In another aspect, the cardiac pacing device 100 further includes an analog-to-digital (AID) data acquisition system 190 configured to acquire analog intracardiac electrogram signals, to convert these raw analog data into digital signals, and to store the digital signals for later processing and/or telemetric transmission to an external device including, but not limited to, an external programmer 104, a bedside monitor 102 and/or a personal advisory module 105. In one aspect, the analog-to-digital (A/D) data acquisition system 190 is coupled to the RA lead 120, the LV lead 124, and the RV lead 130 via the electrode configuration switch 174. In another aspect, the analog-to-digital (A/D) data acquisition system 190, as controlled by control signals 192 received from the microcontroller 160, samples cardiac signals across any pair of desired electrodes via the electrode configuration switch 174.

In an additional aspect, the cardiac pacing device 100 further includes a memory 194 coupled to the microcontroller 160 via a suitable data/address bus 196. In one aspect, the memory 194 is configured to store a plurality of programmable operating parameters used and modified by the microcontroller 160 to customize the operation of the cardiac pacing device 100 to suit the needs of a particular patient. In one aspect, the programmable operating parameters define various aspects of the pacing pulses and impedance detection pulses including, but not limited to, pulse amplitude or magnitude, pulse duration, and electrode polarity. In another aspect, the programmable operating parameters define various aspects of the pacing and/or shocking pulses to be delivered to the patient's heart within a selected tier of therapy including, but not limited to, pacing rate, sensitivity, arrhythmia detection criteria, as well as the amplitude, waveshape and vector of each pacing and shocking pulse to be delivered to the patient's heart. Other non-limiting examples of suitable programmable operating parameters are additional pacing parameters including, but not limited to, base rate, rest rate and circadian base rate.

In one aspect, the cardiac pacing device 100 further includes an impedance measuring circuit 112 configured to receive control signals 114 from the microcontroller 160 and electrode impedance measurements from the electrodes implanted within the heart of the patient. The impedance measuring circuit 112 is configured to obtain various impedance measurements from selected electrodes of the cardiac pacing device 100 via the electrode configuration switch 174 for various uses during the operation of the cardiac pacing device 100. Non-limiting uses of the impedance measuring circuit 112 include the surveillance of lead impedance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; and detecting the opening of heart valves, etc. In one aspect, the impedance measuring circuit 112 is coupled to the implanted electrodes via the electrode configuration switch 174 to enable the selectivity of impedance measurements to any one or more implanted electrode as needed.

In one aspect, the cardiac pacing device 100 further includes a telemetry circuit 101 configured to receive control signals 106 from the microcontroller 160 and to provide a telemetric communication link 103 to one or more external devices including, but not limited to, an external programmer 104, a bedside monitor 102, a personal advisory module 105, and an user input device 150. In one aspect, the telemetry circuit 101 is activated by the microcontroller 160 using the control signal 106.

In one aspect, the operating parameters of the implantable cardiac pacing device 100 may be non-invasively programmed into the memory 194 through the telemetric communication link 103 provided by the telemetry circuit 101 via the external programmer 104 or the bedside monitor 102. Non-limiting examples of suitable external programmer devices include programmers, transtelephonic transceivers, and diagnostic system analyzers. In one aspect, the telemetry circuit 101 enables the transmission of intracardiac electrograms and status information relating to the operation of cardiac pacing device 100 (as contained in the microcontroller 160 or the memory 194) to the external programmer 104, the bedside monitor 102, and/or the personal advisory module 105 through an established communication link 103. Additionally, the telemetry circuit 101 enables communication between the microcontroller 160 and a user input device 150.

Non-limiting examples of a suitable user input device 150 include any suitable user computing device including, but not limited to, a mobile phone, a laptop, a tablet, and a wearable computing device, such as a fitness wearable and "smart glasses". In other aspects, the user input device 150 is any suitable input device, including, but not limited to, a remote control and any other suitable input device specifically configured for communication with the cardiac pacing device 100 to control functionality thereof. In other additional aspects, the user input device 150 includes, but is not limited to, a "smart home controller" or similar Internet of Things device.

In one aspect, the operating parameters of the implantable cardiac pacing device 100 may be non-invasively programmed into the memory 194 through the telemetric communication link 103 provided by the telemetry circuit 101 via the external programmer 104. In various aspects, the external programmer 104 enables a physician or other user to program the operation of the implanted cardiac pacing device 100 and to retrieve and display information received from the implanted cardiac pacing device 100 including, but not limited to, IEGM data and device diagnostic data. In one aspect, the external programmer 104 enables processing and analyzing data received from the implanted cardiac pacing device 100. In this aspect, the processed and analyzed data enable the preliminary diagnosis of medical conditions of the patient and/or the monitoring of the operations of the implanted cardiac pacing device 100.

Figure 8:
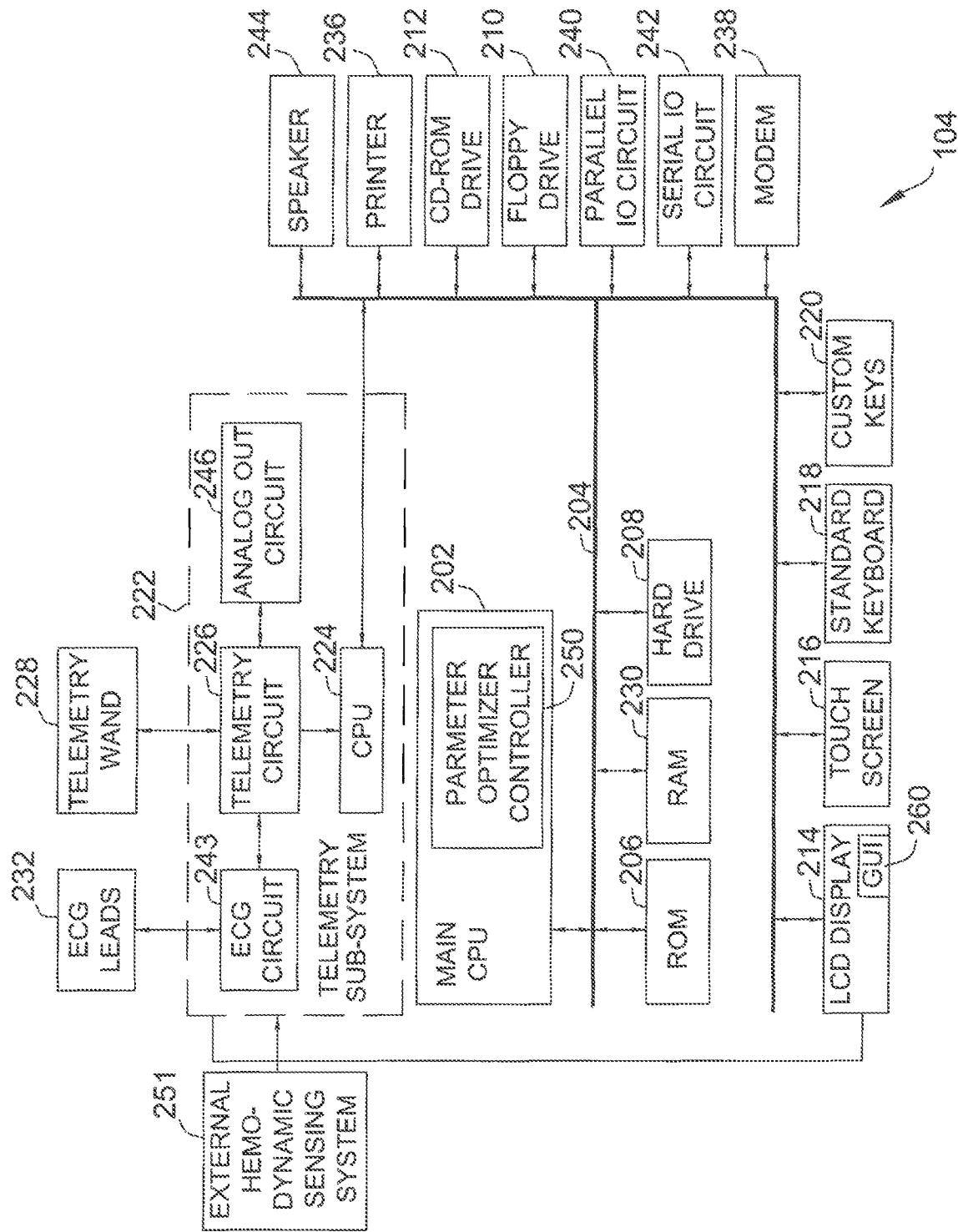
FIG. 8 is a functional block diagram of an external programmer, illustrating the arrangement of elements that provide for the operation, reconfiguration, and parameter optimization of an implanted cardiac pacing device according to one aspect of the disclosure.

FIG. 8 is a schematic illustration of the external programmer 104 in one aspect. The external programmer 104 includes a main CPU 202 configured to enable the operation of the external programmer 104. Non-limiting examples of suitable CPU devices include a programmable microprocessor, a programmable microcontroller, and a dedicated processing device such as an application specific integrated circuit (ASIC) or the like. The external programmer 104 further includes an internal bus 204 configured to access software instructions to be performed by the main CPU 202 via the internal bus 204 from a read only memory (ROM) 206 and a random access memory 230. In one aspect, additional software is accessed, via the internal bus 204, from an additional non-volatile storage medium including, but not limited to, a hard drive 208, a floppy drive 210, a CD ROM drive 212, and any other suitable non-volatile/permanent mass storage device.

In one aspect, the main CPU 202 is configured to display a graphical user interface (GUI) 260 including, but not limited to, a menu of programming options displayed to the physician or other user via an LCD display 214 or other suitable computer display device. In one aspect, the main CPU 202 displays an additional graphical user interface (GUI) 260 including, but not limited to, a menu of specific programming parameters of the implanted device 100 to be programmed, and a menu of types of diagnostic data to be retrieved and displayed. In various aspects, in response to the information contained within the displayed GUI 260, a physician or other user enters various commands to be sent to the main CPU 202 via a user input device including, but not limited to, a touch screen 216 overlaid on the LCD display 214 and/or through a standard keyboard 218 supplemented by additional custom keys 220 including, but not limited to, an emergency VVI (EVVI) key (not shown). In one aspect, depressing the EVVI key activates a safe VVI operational mode with high pacing outputs in the implanted cardiac pacing device 100. In this aspect, inclusion of the EVVI key with the additional custom keys 220 facilitates the selection of a life-sustaining pacing operation in a variety of scenarios.

In one aspect, the external programmer 104 enables the physician or other user to retrieve data stored within the implanted cardiac pacing device 100. In this aspect, the main CPU 202 transmits control signals to a telemetry subsystem 222 configured to facilitate direct communication with the implanted cardiac pacing device 100. In one aspect, the telemetry subsystem 222 includes a dedicated and separate CPU 224 configured to coordinate the operations of the telemetry subsystem 222. The main CPU 202 of the external programmer 104 communicates with the CPU 224 of the telemetry subsystem 222 via the internal bus 204. In various aspects, the telemetry subsystem 222 further includes a telemetry circuit 226 connected to a telemetry wand 228 configured to receive and transmit electromagnetic signals to/from the telemetry circuit 101 of the implanted device 100. In one aspect, the telemetry wand 228 is placed over the chest of the patient near the implanted device 100 to enable reliable transmission of data between the telemetry wand 228 and the implanted device 100.

In various aspects, the external programmer 104 is configured to control the implanted device 100 via control signals generated by the telemetry wand 228. In one aspect, the external programmer 104 is further configured to enable the transmission of additional data in real time as it is detected by the implanted device 100 in response to control signals generated by the telemetry wand 228. Non-limiting examples of patient diagnostic information includes recorded IEGM data, and statistical patient data including as the percentage of paced versus sensed heartbeats. Non-limiting examples of device diagnostic data includes parameters representative of the operation of the implanted device 100 such as lead impedances, battery voltages, battery recommended replacement time (RRT) information and the like. In one aspect, data retrieved from the implanted device 100 is stored by the external programmer 104 within a memory device including, but not limited to, a random access memory (RAM) 230, a hard drive 208 or a floppy diskette (not shown) placed within the floppy drive 210. Additionally, or in the alternative, data may be permanently or semi-permanently stored within a compact disk (CD) or other digital media disk, if the external programmer 104 is provided with a suitable drive device for recording data onto digital media disks, such as a write once read many (WORM) drive (not shown).

In one aspect, detection of the control signals generated by the telemetry wand 228 cause the implanted device 100 to output all previously recorded patient and device diagnostic information to the external programming device 104. Non-limiting examples of data retrieved from the implanted device 100 include parameters representative of the current programming state of the implanted device 100. Under the control of the physician or other user, the external programmer 104 displays the current programming parameters and permits the physician to reprogram these parameters. To this end, the physician enters appropriate commands via any of the aforementioned input devices and, under control of CPU 202, the programming commands are converted to specific programming parameters for transmission to the implanted device 100 via the telemetry wand 228, thereby enabling the reprogramming of the implanted cardiac pacing device 100. In one aspect, the physician may control the external programmer 104, prior to reprogramming specific parameters, to display any or all of the data retrieved from the implanted device 100, including, but not limited to displays of IEGMs and statistical patient information. Any or all of the information displayed by the external programmer 104 may also be printed using a printer 236 in one aspect.

In one aspect, the telemetry subsystem 222 further includes an ECG circuit 243 in communication with ECG leads 232. The ECG circuit 243 is configured to receive and process ECG measurements received from the ECG leads 232. The ECG leads 232 are configured to obtain ECG measurements from the patient with the cardiac pacing device 100 implanted that are analyzed to enable as least a portion of the disclosed method for optimizing the configuration of the cardiac pacing device 100 as described in detail below.

In another aspect, the telemetry subsystem 222 includes an analog output circuit 246 configured to control the transmission of analog output signals, including, but not limited to, emulated ECG signals based on the ECG measurements received by the ECG circuit 243 to be transmitted to an ECG display device (not shown) for display to the physician or other user. Non-limiting examples of suitable ECG display devices include an ECG machine and a chart recorder.

In one aspect, the main CPU 202 further includes a parameter optimizer controller 250 configured to enable the optimization of one or more pacing parameters as described below. In one aspect, the parameter optimizer controller 250 is configured to receive hemodynamic measurements obtained by an external hemodynamic sensing system 251 in communication with the external programmer 104. Non-limiting examples of hemodynamic measurement devices suitable for inclusion as the external hemodynamic sensing system 251 include a Doppler echocardiography system, a nuclear imaging system, an impedance cardiography system, a thermodilution system, and a photoplethysmography system.

In another aspect, the external programmer 104 further includes a modem 238 configured to enable direct transmission of data to other external programmers (not illustrated)

via a public switched telephone network (PSTN) or other interconnection line, including, but not limited to, a T1 line and a fiber optic cable. In one aspect, the modem 238 is connected directly to the internal bus 204 via a data port including, but not limited to, a parallel port 240 and a serial port 242. In various additional aspects, additional peripheral devices may be connected to the external programmer 104 via the parallel port 240 and/or the serial port 242. Non-limiting examples of additional peripheral devices connected to the external programmer 104 in these additional aspects include a speaker 244 and the telemetry subsystem 222. In one aspect, the speaker 244 is configured to deliver audible tones to the user, including, but not limited to, a warning beep in response to an improper input by the physician or user In various aspects, additional input/output (IO) ports are provided as needed to supplement the input/output ports described above. In various aspects, the external programmer 104 enables the physician or other user to retrieve, process, and display a wide range of information received from the implanted device 100 and/or to reprogram the implanted device 100 as needed to enable the disclosed pacing parameter optimization method as disclosed below. The descriptions provided herein with respect to FIG. 8 are intended merely to provide an overview of the operation of the external programmer 104 and are not intended to describe in detail every feature of the hardware and software of the external programmer 104 and is not intended to provide an exhaustive list of the functions performed by the external programmer 104.

In one aspect, the cardiac pacing device 100 further includes and/or is in communication with one or more physiologic sensors 108. The one or more physiologic sensors 108 may include an accelerometer, and may be referred to as "rate-responsive" sensors typically used to adjust the pacing stimulation rate according to the exercise state of the patient. In various aspects, the one or more physiologic sensors 108 include a blood pressure sensor, a heart rate sensor, a temperature sensor, an impedance sensor, an activity sensor, and/or a blood oxygenation sensor. In one aspect, an internal warning device 121 (also referred to as a patient alert) in communication with the microcontroller 160 is provided for generating perceptible warning signals to the patient via vibration, voltage or other methods. The cardiac pacing device 100 additionally includes a battery 110 that provides operating power to the circuits shown in FIG. 2.

In various aspects, the microcontroller 160 includes a plurality of modules configured to enable the monitoring of electrical activity of the heart, the processing of the monitored heart activity to assess the need for electrical cardiac therapy and/or other interventions, and the delivery of electrical pulses and/or shocks as needed to enable one or more therapies and/or other interventions. In one aspect, the microcontroller 160 includes timing control circuitry 161 configured to control the timing of the stimulation pulses, including, but not limited to, pacing rate, atrio-ventricular (AV) delay, interatrial conduction (AA) delay, interventricular conduction (VV) delay and/or intraventricular delay (e.g., LV1-LV2 delay). In other aspects, the timing control circuitry 161 is further configured to monitor timing parameters associated with the operation of the cardiac pacing device 100 including, but not limited to, refractory periods, blanking intervals, noise detection windows, evoked response detection windows, alert intervals, and marker channel timing. In other additional aspects, the timing control circuitry 161 is further configured to track additional durations of time including, but not limited to, a duration of a cardiac pacing therapy including, but not limited to CRT being applied, and a duration of a cardiac pacing therapy including, but not limited to CRT being cancelled or paused by a patient experiencing a cardiac electrical disorder. Referring again to FIG. 2, the microcontroller 160 further includes an arrhythmia detector 162 configured to determine desirable times to administer various therapies.

In additional aspects, the microcontroller 160 further includes a sensing vector controller 169 configured to control the electrode configuration switch 174 via control signals 180 to selectively connect specific electrode(s) to the sensing circuits 182 or 184 as a cathode or anode, to enable the various sensing vectors that are used to obtain intracardiac electrograms (IEGMs) in accordance with the embodiments described herein. In other aspects, multiple sensing vectors are used to obtain a plurality of IEGMs indicative of cardiac electrical activity at a plurality of ventricular regions, and the sensing circuit 184 may include multiple channels (e.g., duplicate circuitry) to enable sensing of more than one ventricular IEGM signal at the same time. In an additional aspect, the sensing circuit 184 may enable time divisional multiplexing to enable sensing more than one ventricular IEGM signal.

In another aspect, additional components of the microcontroller 160 include a cardiac resynchronization therapy (CRT) controller 168 configured to control the delivery of a cardiac pacing therapy including, but not limited to CRT to the patient's heart by the cardiac pacing device 100. CRT, as used herein, describes a cardiac electrical therapy that seeks to normalize asynchronous cardiac electrical activation and the resultant asynchronous contractions by delivering synchronized pacing stimuli to both ventricles using the cardiac pacing device 100. Without being limited to any particular theory, these biventricular pacing stimuli are synchronized to enhance overall cardiac performance and to reduce the patient's susceptibility to life-threatening tachyarrhythmias.

In this other aspect, the CRT controller 168, in cooperation with other elements of the microprocessor 160 including, but not limited to, the timing control circuitry 161, generates one of more control signals including, but not limited to, a control signal 178 delivered to control the operation of the ventricular pulse generator 172 that controls the delivery of the biventricular pacing stimuli via the RV lead 130 and the LV lead 124. In one aspect, the generation of the control signal 178 is influenced by any one or more of a plurality of cardiac pacing control parameters including, but not limited to, atrio-ventricular delay (AVD) interventricular delay (VVD), and the stimulation sites. To synchronize the ventricles and to optimize patient cardiac performance, at least a portion of these cardiac pacing control parameters are adjusted according to a method for cardiac pacing device optimization that makes use of the method for pre-screening candidate cardiac pacing control parameters disclosed herein.

In various aspects, the various components of the microcontroller 160 may be implemented as separate software modules or the separate modules may be combined into a single module configured to perform multiple functions. By way of non-limiting example, the CRT controller 168 and other controllers (not shown) may be combined into a single module. In additional aspects, at least a portion of the components of the microcontroller 160 illustrated as separate components in FIG. 2 may be implemented separately from the microcontroller 160 using additional circuits or devices including, but not limited to, application specific integrated circuits (ASICs) or the like.

Advantageously, the operating parameters of implantable cardiac pacing device 100 may be non-invasively programmed into the memory 194 through a telemetry circuit 101 in telemetric communication with the external programmer 104 or the bedside monitor 102. Non-limiting examples of suitable devices for use as external programmers or bedside monitors include programmers, transtelephonic transceivers, and diagnostic system analyzers. In one aspect, the telemetry circuit 101 is activated by the microcontroller 160 by a control signal 106. The telemetry circuit 101 advantageously enables intracardiac electrograms and status information relating to the operation of the cardiac pacing device 100 (as contained in the microcontroller 160 or the memory 194) to be sent to the external programmer 104, the bedside monitor 102, and/or the personal advisory module 105 through an established communication link 103. Additionally, the telemetry circuit 101 enables communication between the microcontroller 160 and a user input device 150. In various aspects, the user input device 150 is any suitable user computing device including, but not limited to, a mobile phone, a laptop, a tablet, and a wearable computing device, such as a fitness wearable and "smart glasses". In other aspects, the user input device 150 is any suitable input device, including, but not limited to, a remote control and any other suitable input device specifically configured for communication with the cardiac pacing device 100 to control functionality thereof. In other additional aspects, the user input device 150 includes, but is not limited to, a "smart home controller" or similar Internet of Things device. In one aspect, an internal warning device 121 (also referred to as a patient alert) is provided for generating perceptible warning signals to the patient via vibration, voltage or other methods.

II. Method of Cardiac Pacing Device Optimization

In one aspect, the pacing parameters of the cardiac pacing device as described above are optimized using the method for cardiac pacing device optimization that includes a method for pre-screening candidate cardiac pacing device configurations as disclosed herein. This pre-screening method typically includes defining a criterion for determining an equivalent electrical condition for each candidate cardiac pacing device configuration relative to a reference cardiac pacing device configuration. In this aspect, the pre-screening method further includes evaluating a plurality of candidate device configurations at equivalent electrical conditions according to the previously-defined criteria by comparing hemodynamic measurements. Without being limited to any particular theory, the normalization of each candidate device configuration to a reference electrical condition reduces uncertainties in the cardiac pacing device optimization associated with the interdependence of the effects of various pacing parameters on cardiac performance. In one aspect, the candidate cardiac pacing device configuration that enables an optimal cardiac performance based on a comparison of hemodynamic measurements is selected for additional device optimization according to any existing cardiac pacing device optimization method without limitation.

In various aspects, each cardiac pacing device configuration is characterized by a cardiac pacing parameter set that includes at least one cardiac pacing parameter. Any known pacing parameter used to characterize the operation of a cardiac pacing device may be used in the disclosed optimization method without limitation. Non-limiting examples of suitable cardiac pacing parameters suitable for optimization according to the disclosed method include atrioventricular delay (AVD); interventricular delay (VVD); operational mode of the cardiac pacing device, including a dual-chambered mode or a single-chambered mode; pacing base rate; maximum tracking rate; minimum tracking rate; sensitivity with which the cardiac pacing device senses electrical signals within the heart; the amount of electrical energy to be employed in pacing pulses or defibrillation shocks; the type of response to be performed if a pacemaker mediated tachycardia (PMT) or a pm-ventricular contraction (PVC) is detected; whether any rate responsive sensors of the cardiac pacing device, such as minute ventilation sensors, are to be turned on or off; sensor rate; sensor slope; sensor threshold; and any combination thereof. In one aspect, the cardiac pacing device configurations to be optimized by the disclosed cardiac pacing device optimization method are characterized by the cardiac pacing parameter set that includes the atria-ventricular delay (AVD); the site of stimulation by the cardiac pacing device, which may be a single stimulation site or multiple stimulation sites; and the interventricular delay (VVD).

Figure 3:
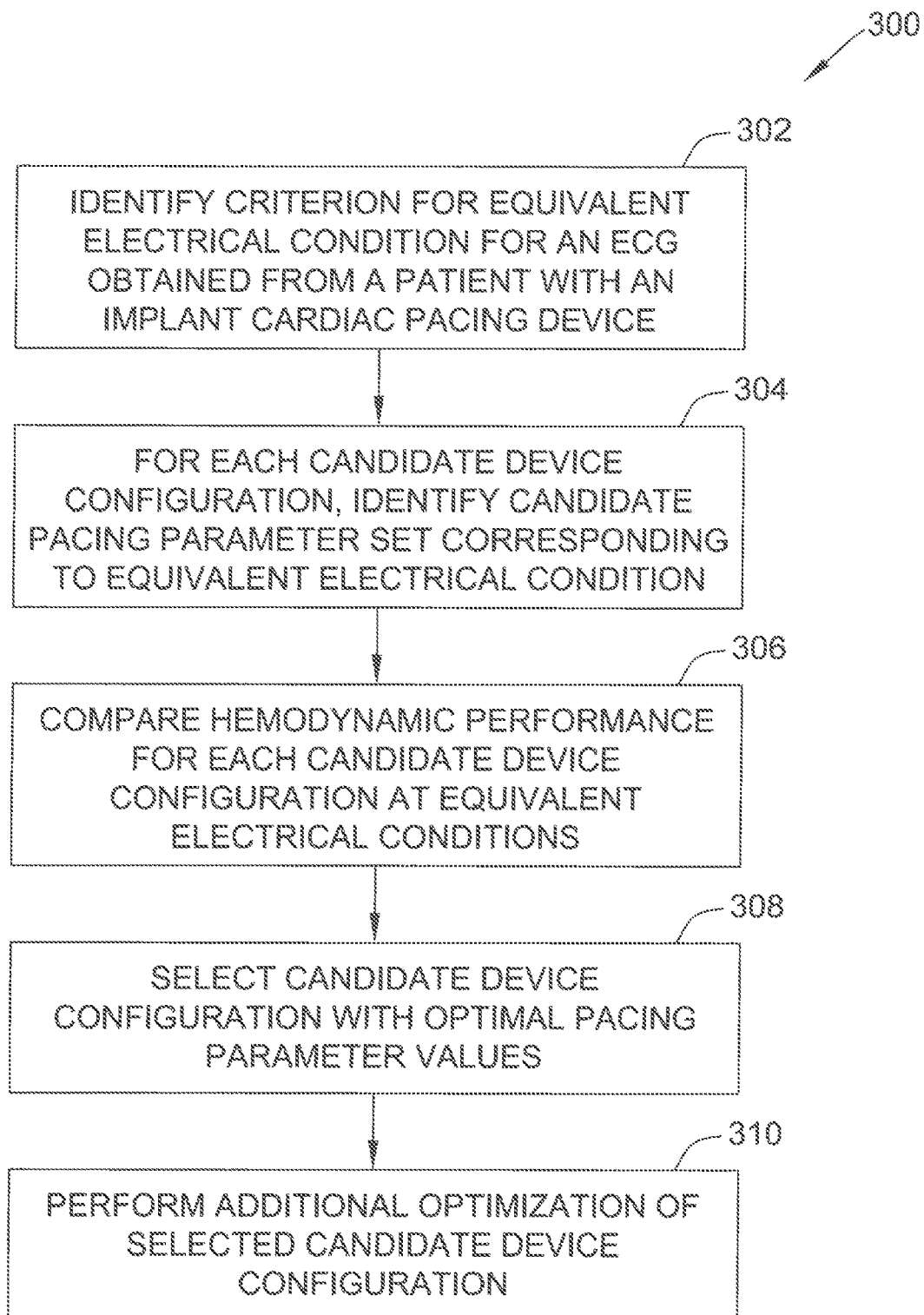
FIG. 3 is a flowchart of a process of cardiac pacing device optimization according to one aspect of the disclosure.

FIG. 3 is a flow chart illustrating a cardiac pacing device optimization method 300 in one aspect. The method 300 includes identifying a criterion for an equivalent electrical condition with respect to a reference device configuration at 302. In various aspects, the criterion for the equivalent electrical condition is defined in terms of a correlation of test ECG measurements obtained for a patient implanted with a cardiac pacing device configured according to a candidate pacing parameter set with respect to a reference ECG measurement obtained for the patient with the cardiac pacing device configured according to a reference pacing parameter set. Without being limited to any particular theory, the comparison of candidate pacing parameter sets classified as electrically equivalent to a reference pacing parameter set normalizes the plurality of candidate pacing parameter sets to the equivalent electrical condition, enabling the comparison of the plurality of candidate cardiac pacing device configurations in the context of a common electrical condition.

Figure 4:
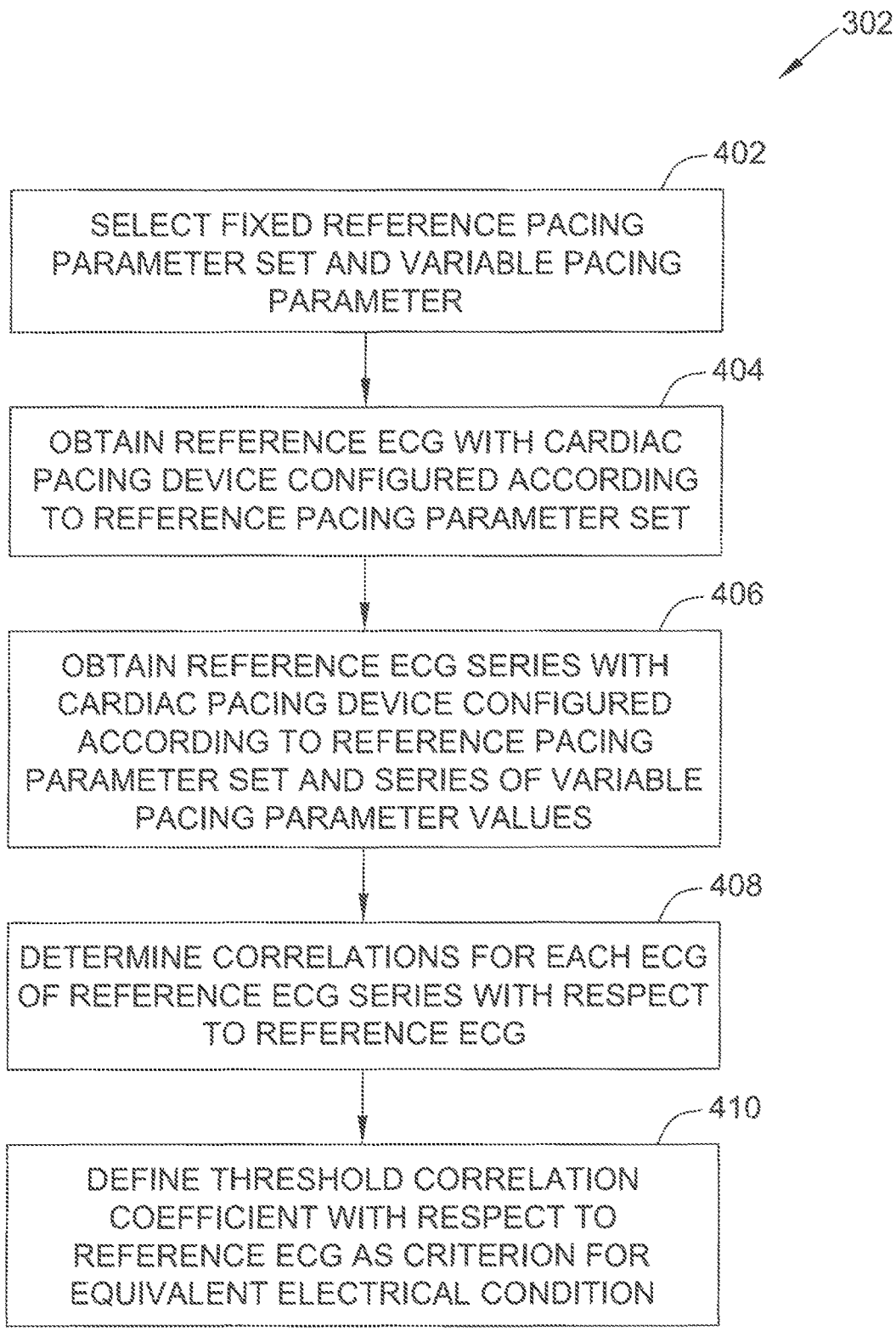
FIG. 4 is a flowchart of a process for identifying a criterion for an equivalent electrical condition for a cardiac pacing device configuration according to one aspect of the disclosure.

FIG. 4 is a block diagram illustrating a method for identifying the criterion for equivalent electrical condition corresponding to step 302 of the cardiac pacing device optimization method 300 illustrated in FIG. 3 in one aspect. Referring again to FIG. 4, the criterion for the equivalent electrical condition is identified by selecting a reference pacing parameter set and a variable pacing parameter at 402. As disclosed above, the reference pacing parameter set characterizes the reference configuration of the cardiac pacing device and provides a common basis of comparison for the plurality of candidate cardiac pacing device configurations to be assessed during device optimization.

In various aspects, any cardiac pacing device configuration may be selected for use as the reference cardiac pacing device configuration without limitation. In one aspect, the reference cardiac pacing device configuration enables fully captured stimulation of the patient's heart rhythm. By way of non-limiting example, the reference cardiac pacing device configuration in this aspect includes fixed reference pacing parameters to define stimulation of the right ventricle only and an atrioventricular delay (AVD) of about 25 msec. In another aspect, the reference cardiac pacing device configuration enables spontaneous heart rhythm in the patient's heart. By way of non-limiting example, the reference cardiac pacing device configuration in this other aspect includes fixed reference pacing parameters to define stimulation of the right ventricle only and an atrioventricular delay (AVD) of about 250 msec ensuring a full spontaneous atrio-ventricular conduction to both ventricles.

In various aspects, the variable pacing parameter includes any of the cardiac pacing parameters disclosed above without limitation. In one aspect, the variable pacing parameter is one of the pacing parameters specified in one or more of the candidate cardiac pacing parameter sets to be assessed using the disclosed cardiac pacing device optimization method 300. In another aspect, the variable pacing parameter is a pacing parameter thought to influence the hemodynamic properties to a relatively higher degree compared to other pacing parameters of the reference cardiac pacing parameter set. In one aspect, the variable pacing parameter is the atrioventricular delay (AVD). Without being limited to any particular theory, the hemodynamic properties of the patient's heart are thought to be particularly sensitive to changes in the value of AVD in the cardiac pacing device.

Referring again to FIG. 4, a reference ECG measurement is obtained for the patient with the cardiac pacing device configured according to the reference pacing parameter set at 404. The reference ECG measurement obtained at 404 defines a baseline reference electrical condition to which subsequent test ECG measurements corresponding to test cardiac pacing device configurations are compared as described below. In one aspect, the reference cardiac pacing parameter set includes stimulation at the right ventricle only, and an AVD of 20 msec, enabling fully captured stimulation of the patient's heart. In another aspect, the reference cardiac pacing parameter set includes stimulation at the right ventricle only, and an AVD of 250 msec, enabling a spontaneous rhythm of the patient's heart. In an example embodiment, the ECG measurement is obtained from surface 12 lead ECG. The ECG measurement is mainly the 12 leads QRS. External ECG systems have the ability to detect QRS and provides a 'template' including 12 temporal windows of the ECG including QRS. In other embodiments, a holter analyzer may be used to classify various cardiac events as PVC, spontaneous events, block cycles, or other specific cardiac cycles.

Referring again to FIG. 4, step 302 of the method 300 further includes obtaining a series of baseline ECGs at 406, in which each baseline ECG of the series includes one value from a series of variable pacing parameter values selected at 404. In one aspect, the series of variable pacing parameter values are AVD values ranging from 25 msec to 250 msec. In this aspect, the 25 msec AVD enables fully captured stimulation and the 250 msec enables spontaneous rhythm of the patient's heart. Each baseline ECG of the series is correlated with the reference ECG measurement obtained at 404 to obtain a series of baseline correlation coefficients at 408. In some embodiments, analyzer software detects all cardiac cycles and makes a classification to create a counter of spontaneous cycles, paced cycles, and PVC. The classification is based on morphology of QRS. In some embodiments, the sensing electrode is used to define the QRS time, predefined windows are then extracted on the 12 leads ECG including the full QRS. A basic cross correlation is calculated on each lead between the reference cycle and test cycle. The average of the 12 cross-correlation value is used. Cross-correlation may be determined using any suitable approach, including methods based on distance or morphology analysis.

Figure 6:
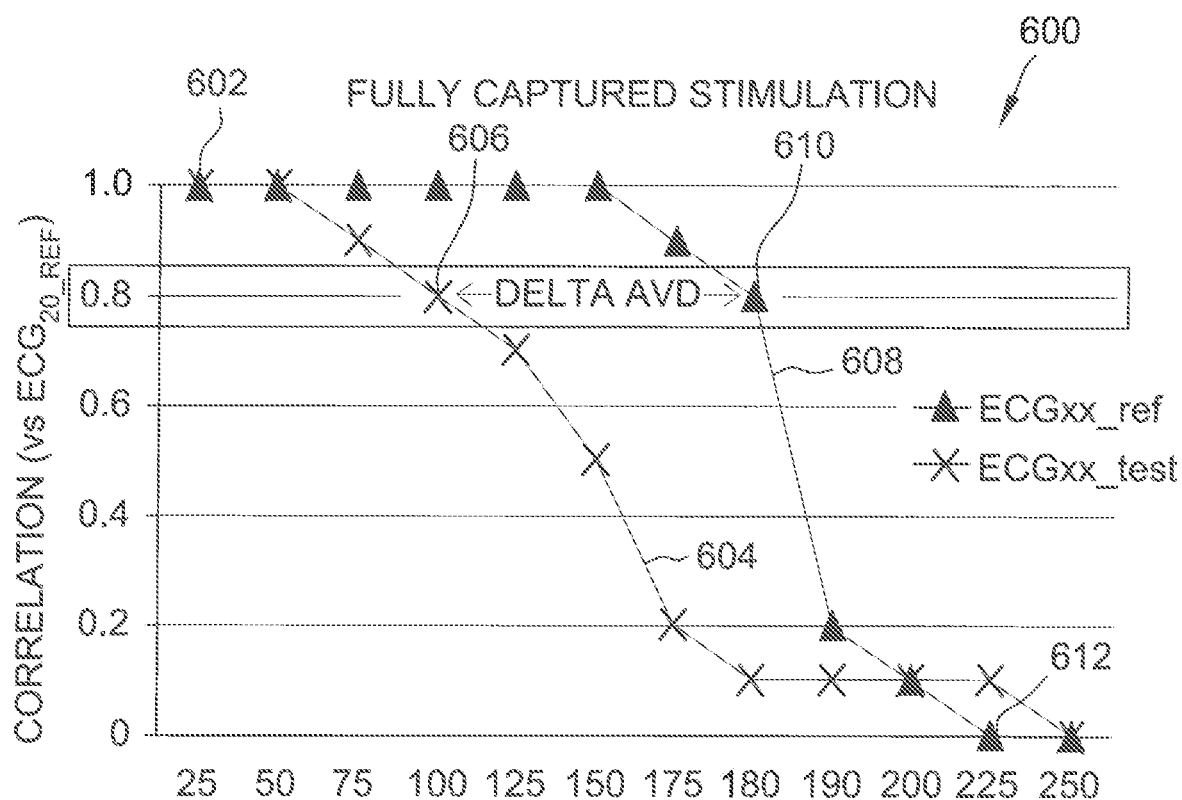
FIG. 6 is a graph summarizing the correlation coefficients obtained for a set of reference ECG measurements and for a set of test ECG measurements, as correlated against a reference ECG representing a fully captured stimulation by a cardiac pacing device according to one aspect of the disclosure.

By way of non-limiting example, FIG. 6 is a graph 600 summarizing the baseline correlation coefficients 608 determined for each baseline ECG measurement from the series of baseline ECG measurements corresponding to the cardiac pacing device configured with RV stimulation only and AVD values ranging from 25 msec to 250 msec. The series of baseline ECG measurements are correlated with the reference ECG measurement, which was obtained with RV stimulation and an AVD of 25 msec. As a result, the baseline correlation coefficient 602 for AVD=25 msec is equal to 1 on the graph 600 of FIG. 6, and decreases to the baseline correlation coefficient 612 of zero at AVD=225-250 msec.

Figure 7:
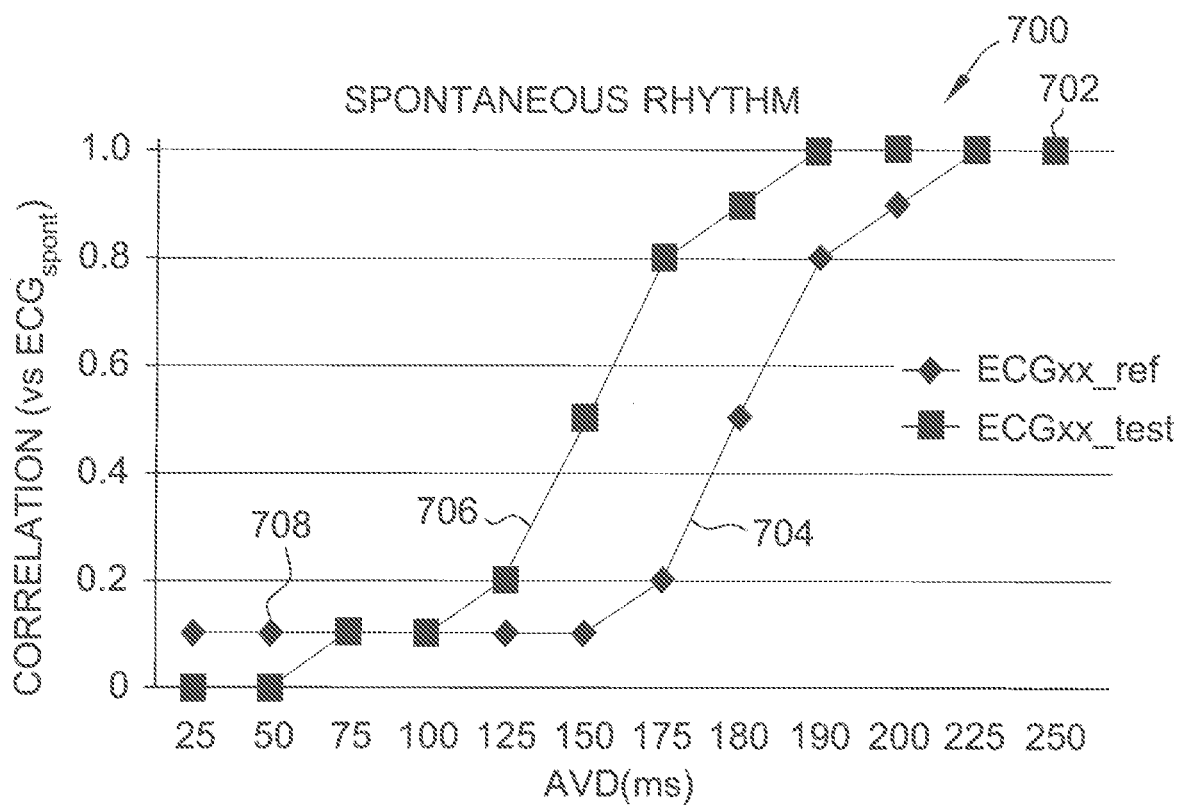
FIG. 7 is a graph summarizing the correlation coefficients obtained for a set of reference ECG measurements and for a set of test ECG measurements, as correlated against a reference ECG representing a spontaneous rhythm configuration of a cardiac pacing device according to one aspect of the disclosure.

By way of another non-limiting example, FIG. 7 is a graph 700 summarizing the baseline correlation coefficients 704 obtained for the series of baseline ECG measurements obtained for the cardiac pacing device configured with RV stimulation only and AVD values ranging from 25 msec to 250 msec. The series of baseline ECG measurements are correlated with the reference ECG measurement, which was obtained with RV stimulation and an AVD of 250 msec. As a result, the baseline correlation coefficient 702 for AVD=250 msec is equal to 1 on the graph 700 of FIG. 7, and decreases to the baseline correlation coefficient 708 of zero at AVD values of 25 msec and 50 msec. At high AVD, the pacing parameters don't impact the ECG because the device is not pacing anymore because a spontaneous event has already happened. Thus, after a certain AVD coefficient will be 1.

Referring again to FIG. 4, the method of identifying the criterion for the equivalent electrical condition further includes defining a threshold correlation coefficient as the criterion for the equivalent electrical condition at 410. In various aspects, the threshold correlation coefficient is typically a relatively high correlation coefficient, corresponding to a relatively high degree of matching between the test ECG measured for a cardiac pacing device with a candidate pacing configuration and the reference ECG when the cardiac pacing device with a candidate cardiac pacing configuration is at an equivalent electrical condition.

In one aspect, the threshold correlation coefficient is at least about 0.5. In various other aspects, the threshold correlation coefficient is at least 0.55, at least 0.6, at least 0.65, at least 0.7, at least 0.8, at least 0.8, at least 0.85, at least 0.9, at least 0.95, at least 0.98, and at least about 0.99. In other additional aspects, the threshold correlation coefficient ranges from about 0.5 to about 0.6, from about 0.55 to about 0.65, from about 0.6 to about 0.7, from about 0.65 to about 0.75, from about 0.7 to about 0.8, from about 0.75 to about 0.85, from about 0.8 to about 0.9, from about 0.85 to about 0.95, and from about 0.9 to 1. By way of non-limiting example, the threshold correlation coefficient is 0.8, as illustrated in FIG. 6.

Referring again to FIG. 3, the cardiac pacing device optimization method 300 further includes identifying a candidate pacing parameter set corresponding to the equivalent electrical condition for each candidate cardiac pacing device configuration at 304. In various applications, identifying the candidate pacing parameter set corresponding to the equivalent electrical condition typically involves obtaining a series of test ECG measurements for patients with the cardiac pacing device in a candidate configuration and performing a correlation analysis similar to the correlation analysis used to identify the criterion for the equivalent electrical condition at 302, as disclosed above.

Figure 5:
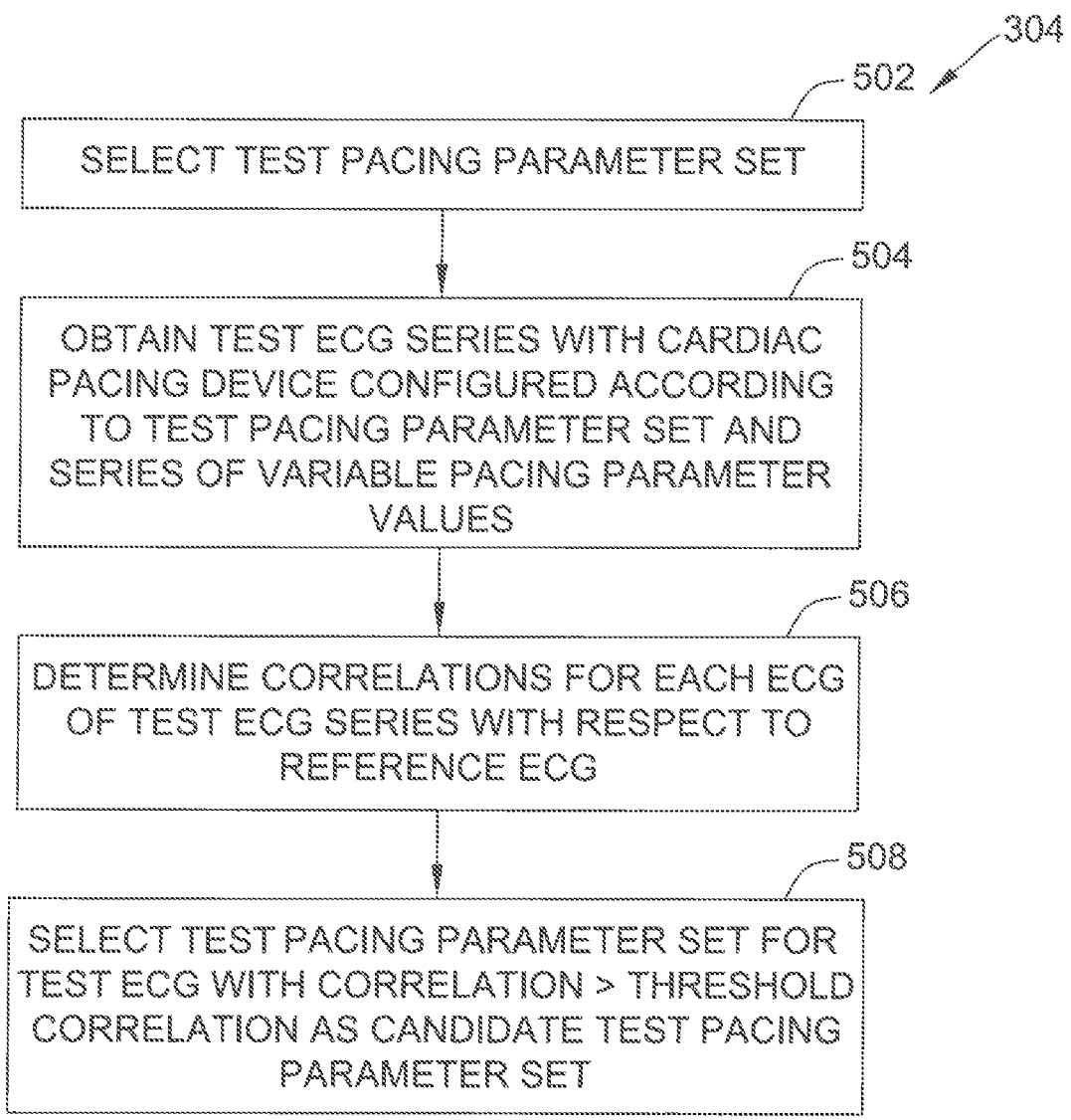
FIG. 5 is a flowchart of a process for identifying a pacing parameter value set for a cardiac pacing device configuration with the equivalent electrical condition as defined by the process of FIG. 4 according to one aspect of the disclosure.

FIG. 5 is a flow chart describing the steps for identifying the candidate pacing parameter set corresponding to the equivalent electrical condition in one aspect, corresponding to step 304 in FIG. 3. Referring again to FIG. 5, a test pacing parameter set is selected at 502. As disclosed above, the test pacing parameter set defines one of the candidate configurations of the cardiac pacing device to be evaluated using the disclosed method 300. A test ECG series is obtained at 504 from the patient with the cardiac pacing device configured according to the test pacing parameter set, in which each test ECG of the series includes one value of the series of variable pacing parameter values described above. Correlations of each test ECG of the series with the reference ECG are determined at 506. The criterion defining the equivalent electrical condition is used to select the test ECG of the series that is electrically equivalent to the reference ECG at 508. In one aspect, the test pacing parameter set with the value of the variable pacing parameter corresponding to the test ECG with the lowest value of correlation coefficient that is greater than or equal to the threshold correlation coefficient is selected as one candidate test pacing parameter set for additional analysis as disclosed below.

By way of non-limiting example, the graph 600 of FIG. 6 further includes a series of test correlations 604 determined for a series of test pacing parameter sets that include a BiV stimulation site (D1 to RV stimulation), an interventricular delay of 30 msec, and AVD values ranging from 25 msec to 250 msec. As illustrated on the graph 600, the correlation coefficient 606 determined for the test ECG obtained with the AVD value of 100 was about 0.8, corresponding to a threshold correlation 610 for electrical equivalence defined using the baseline correlation coefficients 608 as described above. In this non-limiting example, the test ECG with the test pacing parameter set that includes an AVD value of 100 is selected for additional analysis as described herein below.

By way of another non-limiting example, the same test ECGs were correlated with a reference ECG that included right ventricle stimulation only and an AVD of 250 msec, as illustrated in FIG. 7 and as described in a previous non-limiting example disclosed above. The series of test ECGs 706 are highly correlated with the reference ECG at AVD values of 225 msec and 250 msec, indicating that the pacing parameter values (not including AVD) did not significantly alter the spontaneous rhythm properties of the patient's heart. Generally, correlation values above a threshold value indicate similarity, while values below the threshold value indicate non-similarity.

In various aspects, each candidate cardiac pacing device configuration is similarly analyzed using the method 300 at 304 and/or as described in FIG. 5, and the test pacing parameter set classified as electrically equivalent according to the criterion determined by the method 300 at 302 (see FIG. 3 and/or FIG. 4) is stored for subsequent analysis as described below.

In various additional aspects, the method 300 may be optionally repeated for a different selection of variable pacing parameter. By way of non-limiting example, the method 300 may be repeated with intraventricular delay (VVD) selected as the variable pacing parameter. In other additional aspects, the method 300 may be enabled as disclosed above, but with two or more selected variable pacing parameters. In these additional aspects (not shown), the graphs of FIG. 6 and FIG. 7 may be replaced with 3-D contours for one aspect in which two variable pacing parameters are selected, and the graphs of FIG. 6 and FIG. 7 may be replaced with hypersurfaces for another aspect in which three or more variable pacing parameters are selected.

Referring again to FIG. 3, the method 300 further includes, at 306, comparing the cardiac performances of each candidate configuration of the cardiac pacing device at electrically equivalent pacing parameter settings defined according to the method 300 at 304. In one aspect, cardiac performance is quantified as changes in any one or more measured hemodynamic parameters associated with each candidate configuration of the cardiac pacing device. In various aspects, the hemodynamic parameters indicative of cardiac performance are measured using any known hemodynamic measurement device and measurement method without limitation. Non-limiting examples of hemodynamic parameters indicative of cardiac performance include stroke volume; cardiac output; end-diastolic volume; end-systolic volume; ejection fraction; cardiac output index; flow through the mitral valve; maximum rate of change of left ventricular pressure with time; maximum rate of change of aortic pressure with time; mean arterial pressure; arterial pulse pressure; pulmonary capillary wedge pressure; central venous pressure; contractility of the left ventricle, maximum rate of change of pressure with time (i.e. max dP/dt); maximum flow through mitral valve; and vascular volume.

Cardiac performance, as used herein, refers to the measure of the overall effectiveness of the cardiac system of a patient. Stroke volume, as used herein, refers to the amount of blood ejected from the left ventricle during systole. Cardiac output, as used herein, refers to the volume of blood pumped by the left ventricle per minute (alternatively defined as the stroke volume times the heart rate). End-diastolic volume, as used herein, refers to the volume of blood in the chamber at the end of the diastolic phase, when the chamber is at its fullest. End-systolic volume, as used herein, refers to the volume of blood in the chamber at the end of the systolic phase, when the chamber contains the least volume. Ejection fraction, as used herein, refers to percentage of the end-diastolic volume ejected by the ventricle per beat. Cardiac index, as used herein, refers to the volume of blood ejected per minute normalized to the body surface area of the patient. Pulmonary capillary wedge pressure is indicative of filling pressure of the left ventricle. Central venous pressure is indicative of the fluid status of the patient.

In one aspect, stroke volume is measured using a hemodynamic measurement method including, but not limited to, Doppler echocardiography, nuclear imaging, thermodilution, and measurement of dP/dt using a pressure catheter. In another aspect, pulmonary capillary wedge pressure is measured using a hemodynamic measurement device including, but not limited to, a pressure catheter positioned in the pulmonary artery. In an additional aspect, central venous pressure is measured using a pressure catheter positioned in the patient's right ventricle or left atrium. In another additional aspect, vascular volume is measured using vascular photoplethysmography methods. In one aspect, one or more physiologic sensors 108, as illustrated in FIG. 2 and described above, may include the hemodynamic measurement devices used to assess cardiac performance as described above.

Referring again to FIG. 3, the candidate cardiac pacing device configuration determined to impart the most beneficial effects on cardiac performance at 306 is selected as the optimal cardiac pacing device configuration with optimal pacing parameter values at 308. In some aspects, the optimal cardiac pacing device selected at 306 is subjected to additional optimization according to at least one known cardiac pacing device optimization method at 310.

Any known method of cardiac pacing device optimization may be used to enable the additional optimization at 310 of the method 300 without limitation. Non-limiting examples of suitable cardiac pacing device optimization methods include the methods described in U.S. Pat. Nos. 5,487,752; 5,800,471; 7,558,627; 8,781,580; and 9,522,275; as well as U.S. Patent Application Publication No. 2013/0289641, the contents of each of which is incorporated by reference in its entirety.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A method for optimizing pacing parameters of a cardiac pacing device implanted in a patient, the method comprising:
    selecting a reference pacing parameter set and a variable pacing parameter, wherein the reference pacing parameter set comprises a value of the variable pacing parameter;
    measuring a reference ECG associated with the cardiac pacing device configured with the reference pacing parameter set;
    measuring a series of baseline ECGs, each baseline ECG of the series associated with the cardiac pacing device configured with the reference pacing parameter set having a different value of the variable pacing parameter;
    determining a series of baseline correlation coefficients, each baseline correlation coefficient indicative of a correlation between a respective baseline ECG of the series and the reference ECG;
    selecting a threshold correlation coefficient that corresponds to a degree of a match represented by one of the series of baseline correlation coefficients;
    defining the threshold correlation coefficient as a criterion for classifying electrical equivalents to the reference ECG, wherein each baseline ECG associated with a baseline correlation coefficient greater than the threshold correlation coefficient is classified as electrically equivalent to the reference ECG;
    identifying a plurality of candidate pacing parameter sets, wherein each of the plurality of candidate pacing parameter sets is classified as electrically equivalent to the reference ECG due to a correlation coefficient between i) an ECG measured with the cardiac pacing device configured with the candidate pacing parameter set and ii) the reference ECG being greater than the threshold correlation coefficient;
    measuring a plurality of hemodynamic responses of the patient, each hemodynamic response associated with the cardiac pacing device configured with one of the identified candidate pacing parameter sets;
    identifying an optimal hemodynamic response from the plurality of hemodynamic responses;
    selecting a final candidate pacing parameter set corresponding to the optimal hemodynamic response; and
    programming the cardiac pacing device using the final candidate pacing parameter set.

2. The method of claim 1, wherein identifying a plurality of candidate pacing parameter sets comprises:
    selecting a plurality of test pacing parameter sets, each test pacing parameter set comprising at least one test pacing parameter and one value of the variable pacing parameter;
    measuring a series of test ECGs, each test ECG of the series associated with the cardiac pacing device configured with one test pacing parameter set;
    determining a series of test correlation coefficients, each test correlation coefficient indicative of each correlation between each test ECG of the series and the reference ECG; and
    selecting one of the plurality of candidate pacing parameter sets from the plurality of test pacing parameter sets, wherein the one candidate pacing parameter set is a test pacing parameter set of the plurality associated with the minimum test correlation coefficient of the series that is greater than the threshold correlation coefficient.

3. The method of claim 2, wherein the pacing parameters of the plurality of candidate pacing parameter sets, the reference pacing parameter set, the variable pacing parameter, and the plurality of test pacing parameter sets are independently selected from the group consisting of atrioventricular delay (AVD); interventricular delay (VVD); a site of cardiac stimulation; dual-chambered mode of operation, single-chambered mode of operation; pacing base rate; maximum tracking rate; minimum tracking rate; electrode sensitivity; an amount of electrical energy employed in pacing pulses or defibrillation shocks; sensor rate; sensor slope; sensor threshold; and any combination thereof.

4. The method of claim 2, wherein the pacing parameters of the plurality of candidate pacing parameter sets, the reference pacing parameter set, the variable pacing parameter, and the plurality of test pacing parameter sets are independently selected from the group consisting of atrioventricular delay (AVD); site of stimulation by the cardiac pacing device; and interventricular delay (VVD).

5. The method of claim 1, wherein the threshold correlation coefficient is at least about 0.8.

6. The method of claim 5, wherein the threshold correlation coefficient is at least about 0.85.

7. The method of claim 6, wherein the threshold correlation coefficient is at least about 0.9.

8. The method of claim 1, wherein the cardiac pacing device is selected from the group consisting of a pacemaker and a cardioverter-defibrillator device (ICD) device.

9. The method of claim 1, wherein the variable pacing parameter is selected from the group consisting of atrioventricular delay (AVD); interventricular delay (VVD); pacing base rate; maximum tracking rate; minimum tracking rate; electrode sensitivity; an amount of electrical energy employed in pacing pulses or defibrillation shocks; sensor rate; sensor slope; sensor threshold; and any combination thereof.

10. The method of claim 1, wherein the variable pacing parameter is atrioventricular delay (AVD).

11. The method of claim 1, wherein the reference pacing parameter set comprises an atrioventricular delay (AVD) value of about 25 msec, and stimulation at the right ventricle only.

12. The method of claim 1, wherein the variable pacing parameter set comprises a plurality of values of atrioventricular delay (AVD) ranging from about 25 msec to about 250 msec.

13. A system for optimizing pacing parameters of a cardiac pacing device implanted in a patient, the system comprising:
an external hemodynamic sensing system configured to measure a plurality of hemodynamic responses of the patient, each hemodynamic response associated with the cardiac pacing device configured with one candidate pacing parameter set of a plurality of candidate pacing parameter sets of the cardiac pacing device of the patient;
an external ECG sensing system configured to measure ECGs of the patient; and
an external programmer in communication with the cardiac pacing device, the external hemodynamic sensing system, and the external ECG sensing system, the external programmer comprising:
a CPU; and
a computer-readable media encoded with a plurality of modules, each module comprising a set of instructions executable on the CPU, the plurality of modules comprising a parameter optimizer controller configured to:
select a reference pacing parameter set and a variable pacing parameter, wherein the reference pacing parameter set comprises a value of the variable pacing parameter;
receive, from the ECG sensing system, a reference ECG associated with the cardiac pacing device configured with the reference pacing parameter set;
receive, from the ECG sensing system, a series of baseline ECGs, each baseline ECG of the series associated with the cardiac pacing device configured with the reference pacing parameter set having a different value of the variable pacing parameter;
determine a series of baseline correlation coefficients, each baseline correlation coefficient indicative of a correlation between a respective baseline ECG of the series and the reference ECG;
select a threshold correlation coefficient that corresponds to a degree of a match represented by one of the series of baseline correlation coefficients;
define the threshold correlation coefficient as a criterion for classifying electrical equivalents to the reference ECG, wherein each baseline ECG associated with a baseline correlation coefficient greater than the threshold correlation coefficient is classified as electrically equivalent to the reference ECG;
identify the plurality of candidate pacing parameter sets, wherein each of the plurality of candidate pacing parameter sets is classified as electrically equivalent to the reference ECG due to a correlation coefficient between i) a ECG measured with the cardiac pacing device configured with the candidate pacing parameter set and ii) the reference ECG being greater than the threshold correlation coefficient;
configure the cardiac pacing device with each of the plurality of candidate pacing parameter sets;
receive, from the external hemodynamic sensing system, each of the plurality of hemodynamic responses of the patient;
identify an optimal hemodynamic response from the plurality of hemodynamic responses;
select a final candidate pacing parameter set corresponding to the optimal hemodynamic response; and
program the cardiac pacing device using the final candidate pacing parameter set.

14. The system of claim 13, wherein to identify the plurality of candidate pacing parameter sets, the parameter optimizer controller is further configured to:
configure the cardiac pacing device with each of a plurality of test pacing parameter sets, each test pacing parameter set comprising at least one test pacing parameter and one value of the variable pacing parameter;
receive a series of test ECGs from the external ECG sensing system, each test ECG of the series associated with the cardiac pacing device configured with the one test pacing parameter set;
determine a series of test correlation coefficients, each baseline correlation coefficient indicative of each correlation between each test ECG of the series and the reference ECG; and
select one of the plurality of candidate pacing parameter sets from the plurality of test pacing parameter sets, wherein the one candidate pacing parameter set is a test pacing parameter set of the plurality associated with the minimum test correlation coefficient of the series that is greater than the threshold correlation coefficient.

15. The system of claim 13, wherein the threshold correlation coefficient is at least about 0.8.

16. The system of claim 13, wherein the reference pacing parameter set comprises an atrioventricular delay (AVD) value of about 25 msec, and stimulation at the right ventricle only.

17. The system of claim 13, wherein the variable pacing parameter comprises a plurality of values of atrioventricular delay (AVD) ranging from about 25 msec to about 250 msec.

* * * * *